United States Patent
Dinh et al.

(10) Patent No.: US 7,186,254 B2
(45) Date of Patent: Mar. 6, 2007

(54) METHODS AND APPARATUS FOR PROMOTING FUSION OF VERTEBRAE

(76) Inventors: Dzung H. Dinh, 368 E. High Point Rd., Peoria, IL (US) 61614; Marta L. Villarraga, 1709B Green St., Philadelphia, PA (US) 19130

( * ) Notice: Subject to any disclaimer, the term of this patent is extended or adjusted under 35 U.S.C. 154(b) by 534 days.

(21) Appl. No.: 10/357,785

(22) Filed: Feb. 4, 2003

(65) Prior Publication Data
US 2003/0212399 A1    Nov. 13, 2003

Related U.S. Application Data

(60) Provisional application No. 60/359,875, filed on Feb. 25, 2002.

(51) Int. Cl.
*A61B 17/58* (2006.01)
(52) U.S. Cl. ............... 606/61; 606/71; 606/70
(58) Field of Classification Search .......... 606/69, 606/70, 71
See application file for complete search history.

(56) References Cited

U.S. PATENT DOCUMENTS

| | | | |
|---|---|---|---|
| 583,455 A | 6/1897 | Bush | |
| 2,110,414 A | 3/1938 | Bell | |
| 3,426,364 A | 2/1969 | Lumb | |
| 4,096,857 A | 6/1978 | Cramer et al. | |
| 4,289,123 A | 9/1981 | Dunn | |
| 4,309,777 A | 1/1982 | Patil | |
| 4,401,112 A | 8/1983 | Rezaian | |
| 4,657,550 A | 4/1987 | Daher | |
| 4,743,260 A | 5/1988 | Burton | |
| 4,759,769 A | 7/1988 | Hedman et al. | |
| 4,904,263 A | 2/1990 | Buechel et al. | |
| 4,932,975 A | 6/1990 | Main et al. | |
| 5,084,049 A | 1/1992 | Asher et al. | |
| 5,171,278 A | 12/1992 | Pisharodi | |
| 5,236,460 A | 8/1993 | Barber | |
| 5,246,458 A | 9/1993 | Graham | |
| 5,352,225 A | 10/1994 | Yuan et al. | |
| 5,375,823 A | 12/1994 | Navas | |
| 5,390,683 A | 2/1995 | Pisharodi | |

(Continued)

OTHER PUBLICATIONS

Joshi, M.G., et al., "Analysis of a femoral hip prosthesis designed to reduce stress shielding"; Journal of Biomechanics, 2000, pp. 1655-1662, vol. 33.

*Primary Examiner*—Eduardo C. Robert
*Assistant Examiner*—James L. Swiger
(74) *Attorney, Agent, or Firm*—Amster Rothstein & Ebenstein LLP

(57) ABSTRACT

Methods and apparatuses for promoting fusion of vertebrae are provided. The apparatuses comprise interconnecting plates that fixate vertebrae to each other and provide for a predetermined amount of subsidence where the fusion occurs. Allowing for this predetermined amount of subsidence increases bone to bone contact at the graft, which promotes fusion without having excessive settling of the two vertebrae onto the graft. The predetermined amount of subsidence is achieved by the placement of a plate spacer between each of two interconnecting plates when the plates are attached to the vertebrae. The plate spacer has a height equal to the maximum amount of subsidence desired. After affixing the plates to the vertebrae, the plate spacer is removed, leaving a space between the plates, which allows the vertebrae to subside by a distance equal to the height of the plate spacer.

15 Claims, 18 Drawing Sheets

U.S. PATENT DOCUMENTS

| | | |
|---|---|---|
| 5,458,641 A | 10/1995 | Ramirez Jimenez |
| 5,484,439 A | 1/1996 | Olson et al. |
| 5,571,109 A * | 11/1996 | Bertagnoli .................. 606/61 |
| 5,603,713 A | 2/1997 | Aust et al. |
| 5,616,142 A * | 4/1997 | Yuan et al. .................. 606/61 |
| 5,653,763 A | 8/1997 | Errico et al. |
| 5,672,175 A | 9/1997 | Martin |
| 5,672,177 A | 9/1997 | Seldin |
| 5,683,465 A | 11/1997 | Shinn et al. |
| 5,693,100 A | 12/1997 | Pisharodi |
| 5,700,264 A | 12/1997 | Zucherman et al. |
| 5,752,955 A | 5/1998 | Errico |
| 5,827,328 A | 10/1998 | Buttermann |
| 5,843,082 A | 12/1998 | Yuan et al. |
| 5,865,846 A | 2/1999 | Bryan et al. |
| 5,865,848 A | 2/1999 | Baker |
| 5,885,284 A | 3/1999 | Errico et al. |
| 5,916,267 A | 6/1999 | Tienboon |
| 6,015,436 A | 1/2000 | Schönhöffer |
| 6,080,193 A | 6/2000 | Hochshuler et al. |
| 6,093,205 A | 7/2000 | McLeod et al. |
| 6,102,950 A | 8/2000 | Vaccaro |
| 6,110,210 A | 8/2000 | Norton et al. |
| 6,258,125 B1 | 7/2001 | Paul et al. |
| 6,306,136 B1 * | 10/2001 | Baccelli ..................... 606/61 |
| 6,328,738 B1 | 12/2001 | Suddaby |
| 6,402,756 B1 * | 6/2002 | Ralph et al. ................ 606/71 |
| 6,533,786 B1 | 3/2003 | Needham et al. |
| 6,932,820 B2 * | 8/2005 | Osman ....................... 606/71 |
| 7,008,427 B2 * | 3/2006 | Sevrain ...................... 606/71 |
| 2004/0019353 A1 | 1/2004 | Freid et al. |
| 2004/0092939 A1 | 5/2004 | Freid et al. |

* cited by examiner

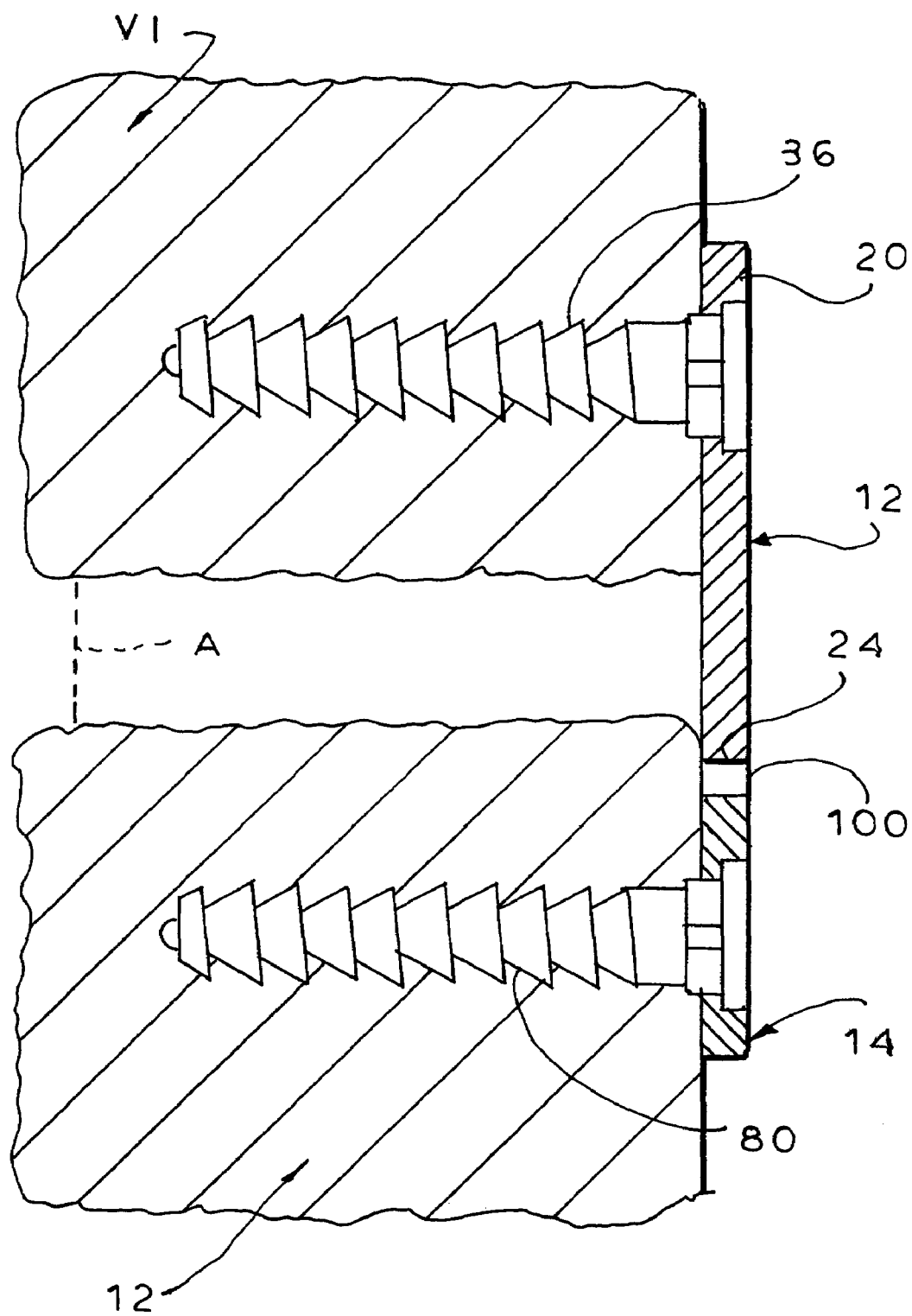

FIG. 5
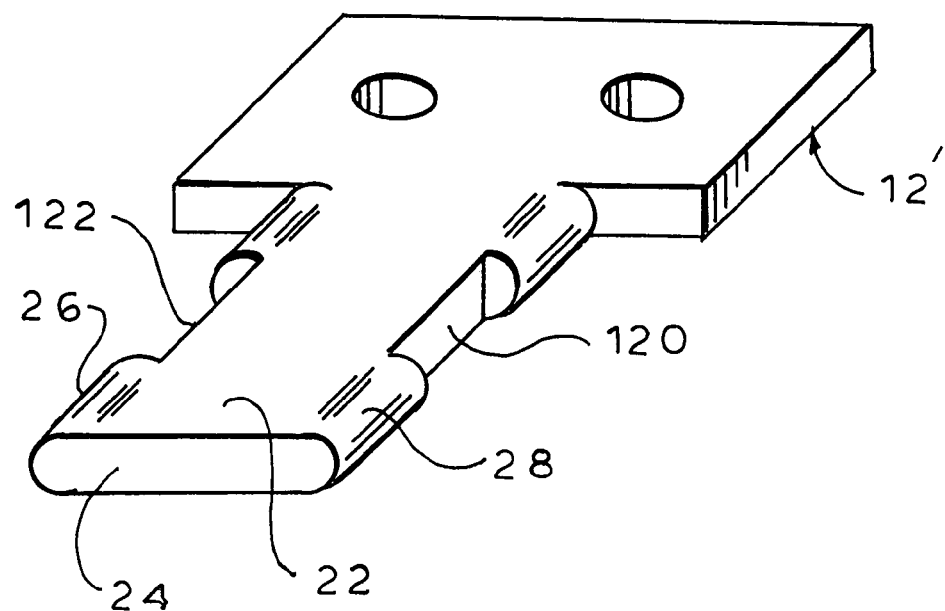
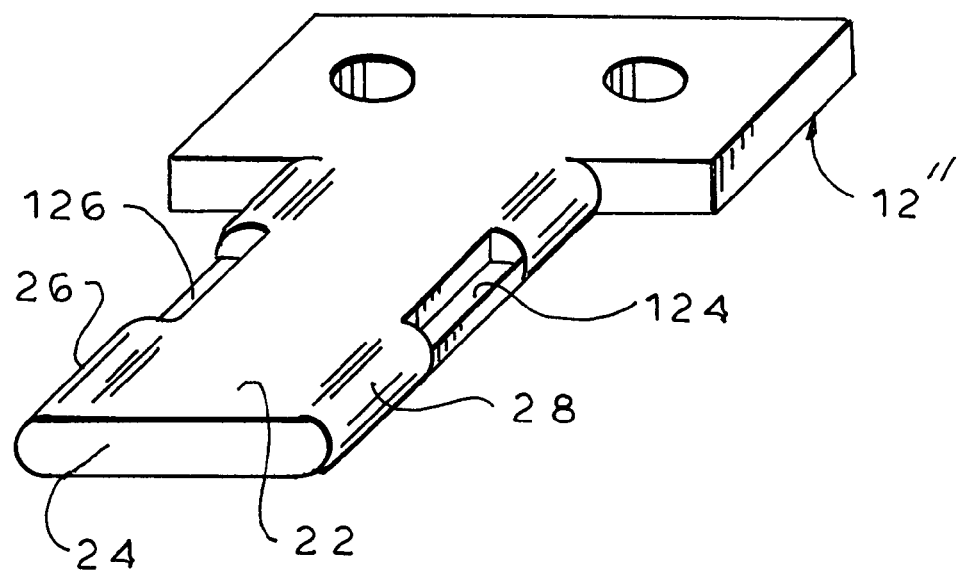
FIG. 6

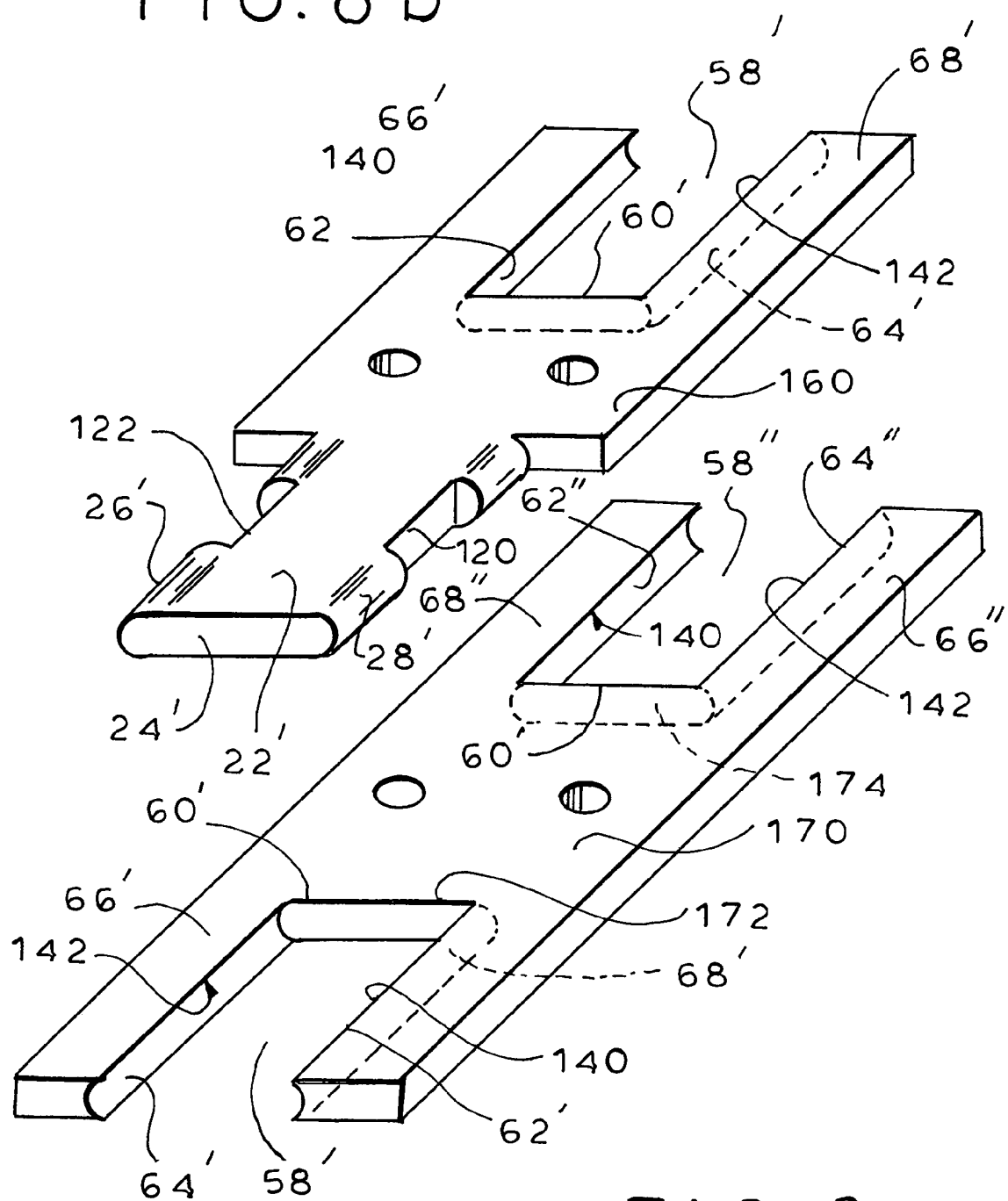

METHODS AND APPARATUS FOR PROMOTING FUSION OF VERTEBRAE

CROSS-REFERENCE TO RELATED APPLICATION

This application claims the benefit of U.S. Provisional Application 60/359,875, filed Feb. 25, 2002.

BACKGROUND (1) Field of the Invention

The present invention relates to methods and apparatuses for stabilizing vertebrae when fusing the vertebrae.

(2) Description of the Related Art

Fusion of vertebrae is often necessary to relieve debilitating pain or correct a deformity. When vertebrae are fused, e.g., with bone grafts, graft extenders, or interbody spacers such as interbody cages or boxes (collectively termed "grafts" herein), it is desirable to stabilize the fused vertebrae using an apparatus such as a plate to fixate one cervical vertebra to another to promote fusion across motion segments.

There are various known apparatuses useful for stabilizing vertebrae when the vertebrae are fused. See, e.g. U.S. Pat. Nos. 4,743,260; 5,603,703; 5,458,641; 5,827,328; and 6,080,193.

The known apparatuses are generally useful to prevent horizontal displacement of the two grafted vertebrae. They also can prevent excessive compression of the two vertebrae, which can lead to a weak fusion or even collapse of the graft. However, the apparatuses can also lead to stress shielding, in which fusion of the vertebrae to the grafted bone is impeded or prevented entirely because the apparatus prevents adequate contact between the vertebra and the graft. Resorption of the bone graft can exacerbate this problem. It is well known in the art that some subsidence, or settling, between the vertebrae at the graft is advantageous to quickly forming a strong fusion. The subsidence increases bone to bone contact, which is well known to enhance bone fusion, as predicted by Wolff's law, by enhancing physiological processes involved in bone remodeling (Kowalski et al., 2001, Neurol. Focus 10 (4) Article 2).

The problem of stress shielding is partially addressed in U.S. Pat. No. 5,843,082, which provides an apparatus having a plate on each vertebra, and a pair of longitudinal rods which interconnect the plates. The plates can slide along the rods vertically, which allows for subsidence between the vertebrae. There is no suggestion therein that the amount of subsidence could or should be controlled using that apparatus. Thus, while the apparatus in the '082 patent does not cause stress shielding, it also does not prevent excessive subsidence.

It is therefore an object of the present invention to provide improved apparatuses and methods for promoting optimal fusion at a graft, particularly at cervical vertebrae.

It is a further object of the invention to provide improved apparatuses and methods for stabilizing the fusion that minimize stress shielding.

It is an additional object of the invention to provide apparatuses and methods for minimizing stress shielding as well as excessive subsidence at vertebral fusions, thus promoting optimal fusion at the graft.

It is a still further object of the invention to provide an apparatus that accomplishes the above objects yet is compact in size and utilizes a minimum amount of parts.

SUMMARY OF THE INVENTION

It has been found that the above and related objects of the present invention are obtained by the use of slidably interconnected plates that fixate vertebrae to each other and provide for a predetermined amount of subsidence at the fusion site. This predetermined subsidence increases bone to bone contact at the graft, which promotes fusion without having excessive compression of the two vertebrae onto the graft. The predetermined subsidence is achieved by the placement of a plate spacer between each of two interconnecting plates when the plates are attached to the vertebrae. The plate spacer has a height equal to the amount of subsidence desired. After affixing the plates to the vertebrae, the plate spacer is removed, leaving a space between the plates, which allows the vertebrae to subside by a distance equal to the height of the plate spacer.

Accordingly, in some embodiments, the present invention is directed to apparatuses for promoting fusion of a first vertebra and a second vertebra in a spinal column at a graft between the first vertebra and the second vertebra.

A preferred embodiment of these apparatuses comprises a first plate mountable to the first vertebra, and a second plate mountable to the second vertebra. The first plate comprises integral means for slidably interconnecting with the second plate, the sliding occurring parallel to the long axis of the spinal column. The means for slidably interconnecting the first and second plates prevents rotational and transverse movement of the first vertebra relative to the second vertebra.

Preferably, the first plate has a first base mountable to the first vertebra and a tongue protruding from the first base with an end distal to the first base and two sides perpendicular to the end. Also, the second plate has a second base with two sides and a top. The second base is capable of attachment to the second vertebra, and the second plate has a groove formed by the top of the second base and inner edges of the two sides of the second base. In these embodiments, the tongue of the first plate and the groove of the second plate slidably interconnect when attached to the first and second vertebrae, the interconnection occurring at the two sides of the tongue of the first plate and the inner edges of the two sides of the groove of the second plate. Additionally, the end of the tongue and the top of the second base are capable of touching, preventing compression of the first vertebra with the second vertebra at the graft between the two.

These apparatuses preferably also comprise a removable plate spacer suitable for placing between the first plate and the second plate.

In additional preferred embodiments of the apparatuses, the apparatus comprises a first member for attachment to the first vertebra and a second member for attachment to the second vertebra, along with a means for attaching the apparatus to the first vertebra at the first member, a means for attaching the apparatus to the second vertebra at the second member, a means for preventing rotational and transverse movement of the first vertebra relative to the second vertebra, and a plate spacer comprising a height, where the plate spacer is capable of insertion into the apparatus between the first member and the second member. In these embodiments, the plate spacer can be removed from the apparatus after the apparatus is attached to both the first vertebra and the second vertebra, and the height of the plate spacer provides a subsidence between the two vertebrae upon removal of the plate spacer, the subsidence being equivalent to the height of the plate spacer.

In still other preferred embodiments, the invention is directed to apparatuses for promoting fusion of a first vertebra and a second vertebra in a spinal column at a graft between the first vertebra and the second vertebra. The apparatuses comprise a first plate mountable to the first vertebra, a second plate mountable to the second vertebra, and a removable plate spacer suitable for placing between the first plate and the second plate, where the plate spacer comprises a height. In these embodiments, the first plate comprises an integral means for slidably interconnecting with the second plate, where the sliding occurs parallel to the long axis of the spinal column. This means prevents rotational and transverse movement of the first vertebra relative to the second vertebra. The apparatuses of these embodiments further comprise a means for limiting axial extension of the first plate with respect to the second plate.

The invention is also directed to apparatuses for promoting fusion of a first vertebra, a second vertebra and a third vertebra in a spinal column at grafts between (a) the first vertebra and the second vertebra and (b) the second vertebra and the third vertebra. The apparatuses comprise a first plate mountable to the first vertebra, a second plate mountable to the second vertebra, and a third plate mountable to the third vertebra. In these embodiments, the first plate and the third plate comprise integral means for slidably interconnecting with the second plate, where the sliding occurs parallel to the long axis of the spinal column. This means prevents rotational and transverse movement of the first vertebra relative to the second vertebra and the second vertebra relative to the third vertebra.

In related embodiments, the invention is directed to apparatuses for promoting fusion of n adjacent vertebrae in a spinal column at grafts between each of the n vertebrae. The apparatuses comprise n plates, each plate mountable to one of each of the n vertebrae. Each plate also comprises integral means for slidably interconnecting with adjacent plate(s), where the sliding occurs parallel to the long axis of the spinal column. This means prevents rotational and transverse movement of each of the n vertebrae relative to each adjacent vertebra(e) of the n vertebra.

The above apparatuses are useful in methods for promoting fusion of a first vertebra with a second vertebra in a spinal column. A preferred embodiment of the methods comprises providing an apparatus, the apparatus comprising a means for attaching the apparatus to the first vertebra at a first member; a means for attaching the apparatus to the second vertebra at a second member; a means for preventing rotational movement of the first vertebra relative to the second vertebra; and a plate spacer comprising a height. The plate spacer is capable of insertion into the apparatus between the first member and the second member such that the plate spacer can be removed from the apparatus after the apparatus is attached to both the first vertebra and the second vertebra. In these methods, the apparatus is attached to the first vertebra at the first member; the means for preventing rotational displacement of the first vertebra from the second vertebra is partially engaged; the plate spacer is placed between the first member and the second member; the means for preventing rotational displacement is substantially fully engaged such that the first member and the second member each abut the plate spacer; the apparatus is attached to the second vertebra at the second member; and the plate spacer is removed from between the first member and the second member.

The invention is also directed to any of the novel plates used in any of the above apparatuses and methods, including but not limited to the following: (a) a plate with a base mountable to the vertebra, the plate also having a tongue protruding from the base with an end distal to the base and two sides perpendicular to the end; (b) a plate with a base mountable to the vertebra, the base having two sides and a top, the plate having a groove formed by a top of the base and inner edges of the two sides of the base; (c) a plate with a base mountable to the vertebra, the plate also having a first tongue protruding from the base with an end distal to the base and two sides perpendicular to the end, the plate also having a second tongue protruding from the base with an end distal to the base and two sides perpendicular to the end, wherein the first tongue and the second tongue are directed in opposite directions along the long axis of the spinal column; (d) a plate with a base mountable to the vertebra, the plate also having a tongue protruding from the base with an end distal to the base and two sides perpendicular to the end, the plate also having a groove formed by a top of the base and inner edges of the two sides of the base, wherein the tongue and the groove are directed in opposite directions along the long axis of the spinal column; and (e) a plate with a base mountable to the vertebra, the base having two sides, a top and a bottom, the plate having a first groove formed by the top of the base and inner edges of the two sides of the base, the plate also having a second groove formed by the bottom of the base and inner edges of the two sides of the base, wherein the first groove and the second groove are directed in opposite directions along the long axis of the spinal column.

BRIEF DESCRIPTION OF THE DRAWING

These and other objects, features and advantages of the present invention will be more fully understood by reference to the following detailed description of the presently preferred, albeit illustrative, embodiments of the present invention wherein:

FIG. 3 is a view of the apparatus of FIG. 1, taken along the sagittal plane as indicated by line 3—3 in FIG. 1.

FIG. 5 is a view of an alternative embodiment of plate 12 illustrated in FIGS. 1–3.

FIG. 6 is a view of an additional alternative embodiment of plate 12 illustrated in FIGS. 1–3.

FIGS. 8a, 8b and 8c are views of three plates constructed in accordance with the present invention useful for stabilizing three or more vertebrae.

DETAILED DESCRIPTION OF THE PREFERRED EMBODIMENTS OF THE INVENTION

Figure 1:
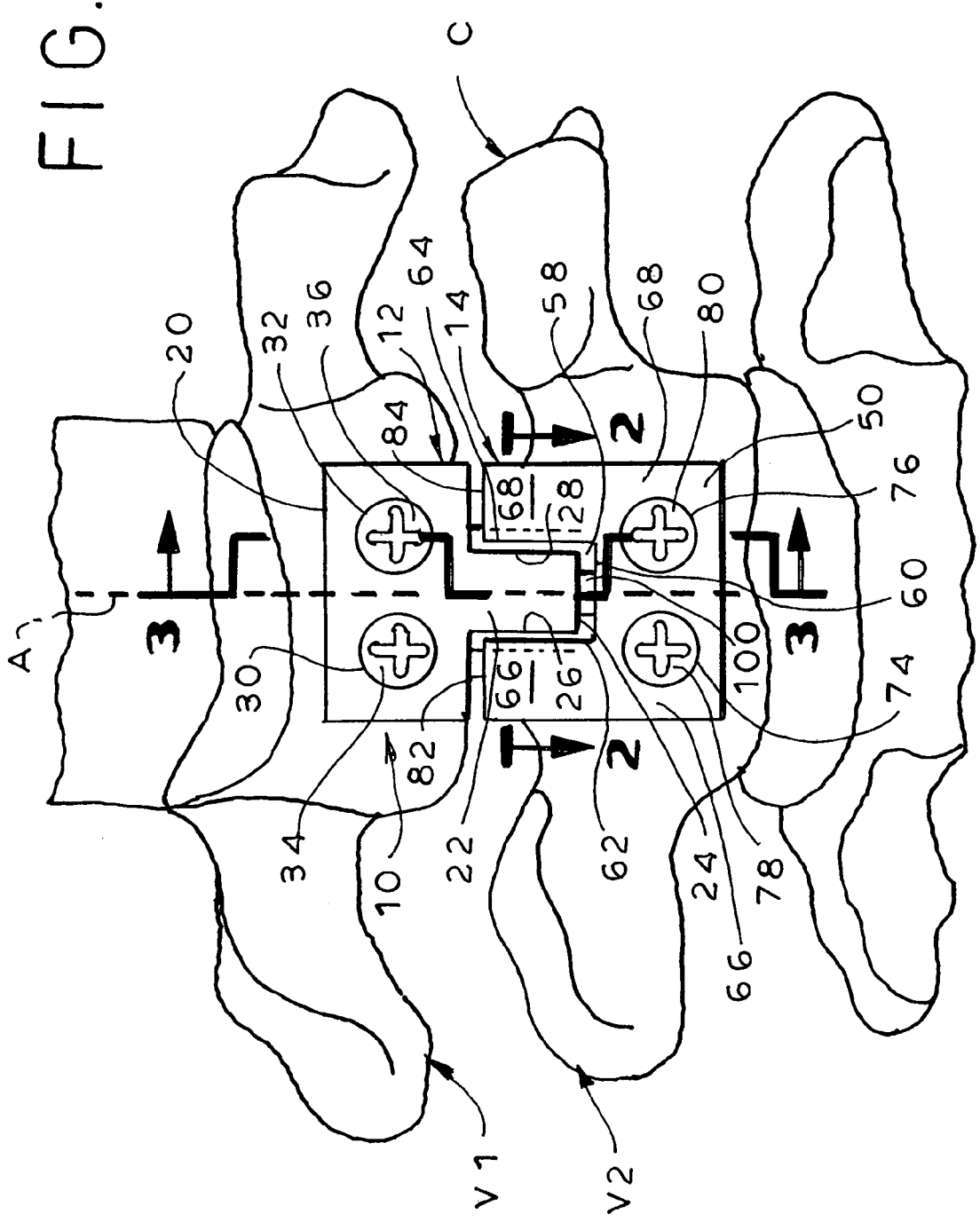
FIG. 1 is an elevational view of an apparatus constructed in accordance with the present invention for stabilizing two vertebrae, as seen before removal of the plate spacer.

The present invention provides methods and apparatuses for stabilizing vertebrae while simultaneously minimizing stress shielding and excessive subsidence. To achieve this, apparatuses are utilized that have at least two separate members, one member being attached to each of the vertebrae. The members that are adjacent to each other can be interconnected to prevent rotational and transverse displacement of the two vertebrae in relation to each other. Additionally, the apparatuses preferably include plate spacer(s) of a preselected height that is placed between each two adjacent members when the members are attached to the vertebrae, such that the members are separated by the height of the plate spacer. After attachment of the members to the vertebrae, the plate spacer(s) is/are removed. This allows for subsidence of the each two adjacent vertebrae by a distance equal to the height of the plate spacer. Thus, stress shielding as well as excessive subsidence is minimized.

In preferred embodiments, the methods and apparatuses are used for fusion of cervical vertebrae, because the problem of stress shielding is encountered most often in cervical fusions. However, the methods and apparatuses are also capable of use for fusion of thoracic or lumbar vertebrae.

In some embodiments, the vertebrae to which the apparatuses are attached are preferably adjacent to each other. However, the apparatuses can be designed and utilized to span and stabilize three or more vertebrae.

Referring now to the drawing, and in particular to FIGS. 1 through 4 thereof, a preferred embodiment of the apparatuses of the invention is illustrated. This apparatus has two plates, one comprising a tongue, and the other comprising a groove. The tongue and groove interconnect and slide. Each of the plates is secured to a respective vertebra by two screws or similar fasteners such as anchors, etc, as are known in the art. Specifically, FIGS. 1–4 illustrate an apparatus 10 for use in retaining bone portions such as cervical vertebrae V1 and V2 of a human spinal column C to stabilize the vertebrae with respect to each other rotationally and along the vertical axis A. The apparatus comprises a first plate 12, attached to V1, and a second plate 14, attached to V2. These plates, and the screws used to attach them to vertebrae are surgically implantable and are made of a suitable biocompatible material, such as titanium, titanium alloy, or stainless steel.

As best shown in FIG. 1, the first plate 12 has a base 20 and a tongue 22 protruding from the base 20. The tongue 22 comprises an end 24 distal to the base 20 and two sides 26, 28 perpendicular to the end 24. The first plate also has two holes 30, 32 which accommodate screws 34, 36, used to attach the first plate to vertebra V1. Although two holes which accommodate screws that project perpendicularly is shown in the figures, the apparatus is not limited to such an arrangement. Any appropriate arrangement of screw types, hole types, and hole numbers is contemplated as being within the scope of the invention. Thus, the first plate can comprise three or more holes to provide for three or more screws into the vertebra, and, although the screw holes 30, 32 shown in FIG. 1 accommodate screws that project perpendicularly from the plane of the first plate 12, they can be designed to accommodate screws that are at an appropriate angle to provide for a secure attachment to the vertebra V1. Additionally, a locking device to secure the screws can optionally be incorporated into these apparatuses. Appropriate devices are well known in the art.

Vertebra V1, to which the first plate 12 is attached, is shown in FIG. 1 as superior to vertebra V2 in the spinal column C. However, vertebra V1 could also be inferior to vertebra V2 in the spinal column C, in which case the first plate 12 is affixed into V2 with the tongue protruding upward toward V1. In either case, the first plate 12 is aligned and screwed into the vertebra such that the tongue 22 is protruding toward vertebra V2. Thus, when vertebra V2 is below vertebra V1, the tongue 22 is protruding downward. Conversely, when vertebra V1 is below vertebra V2, the tongue 22 is protruding upward.

The second plate 14 has a base 50 and a groove 58. The groove 58 is formed by an edge 60 at the top of the base 50 and inner edges 62, 64 of sides 66, 68 protruding from the two sides of the base 50. The sides of the groove 66, 68 also each have a top 82 and 84, respectively. The second plate 14 also is shown in FIG. 1 as having two holes 74, 76 which accommodate screws 78, 80. As with the first plate, the type, number and projection angle of screws that anchor the second plate to the vertebra are merely shown as illustrative, and can be substituted by known methods as appropriate.

Figure 2:
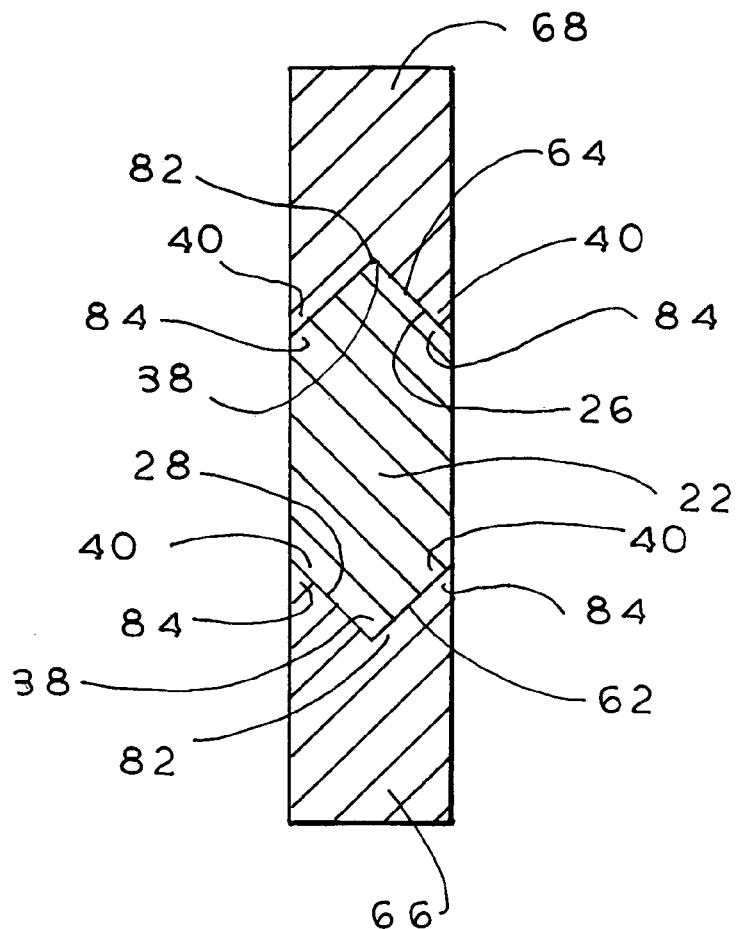
FIG. 2 is a cross sectional view of the apparatus of FIG. 1, showing the interconnection between the two plates at the tongue and groove sections located on line 2—2 in FIG. 1.
Figure 2A:
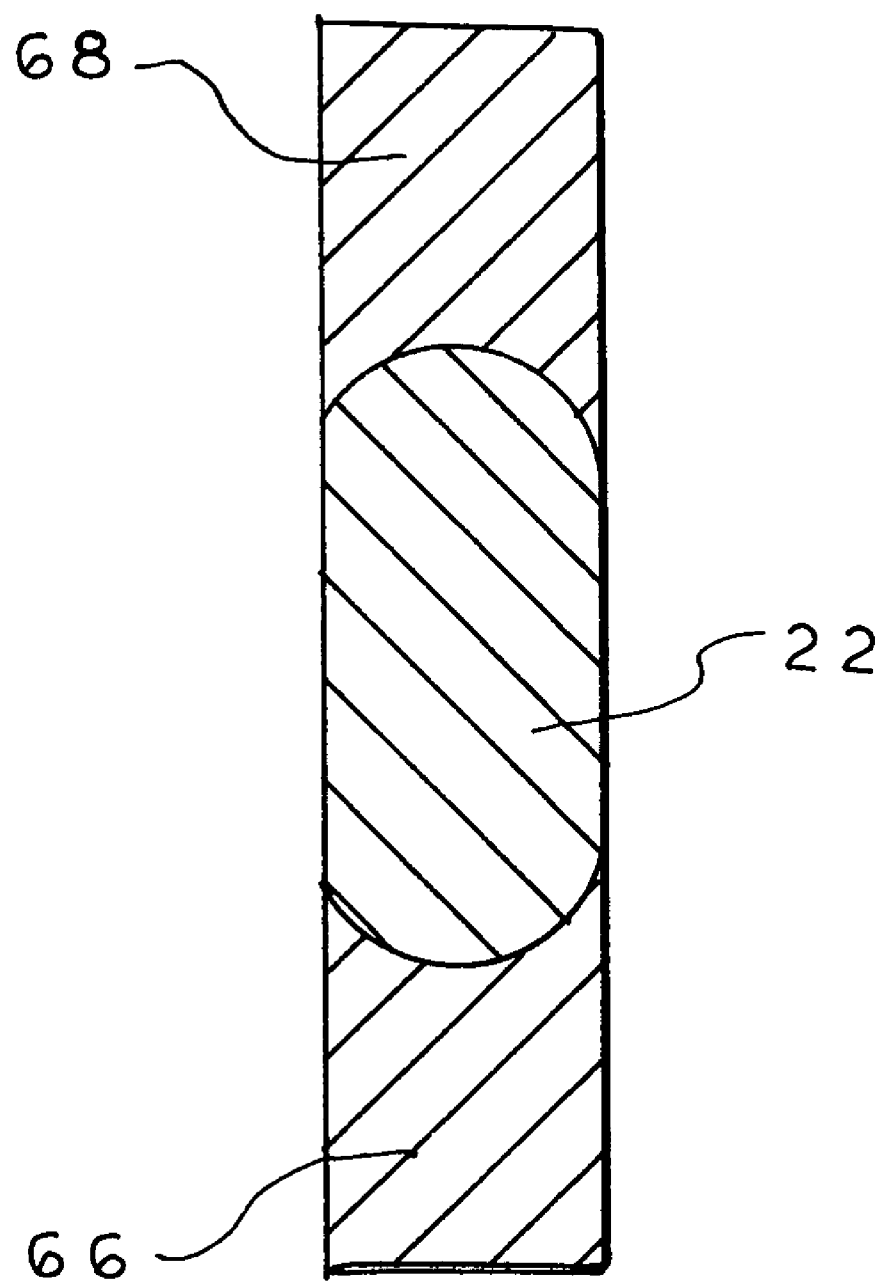
FIG. 2a shows an alternate form suitable for interconnecting the two plates.
Figure 7A:
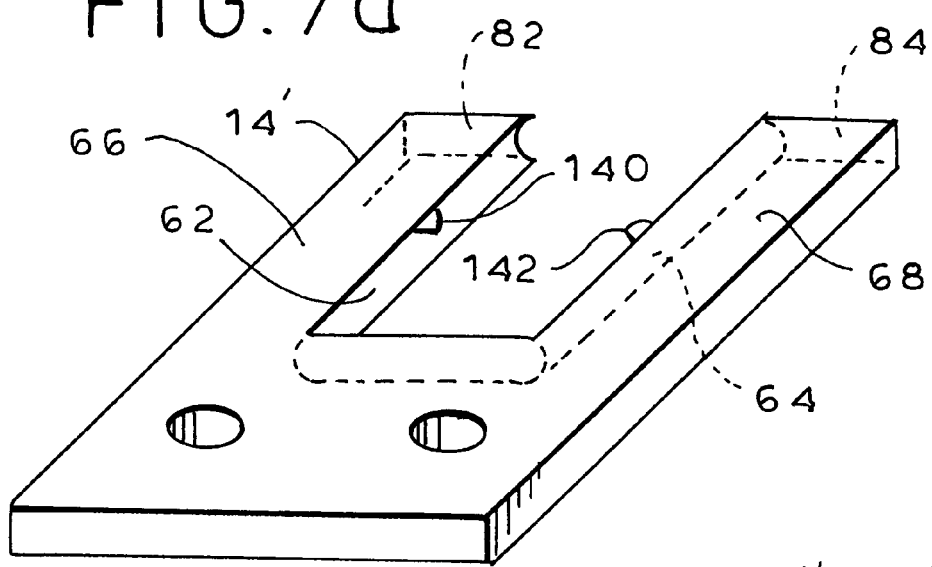
FIGS. 7a and 7b are views of alternative embodiments of plate 14 illustrated in FIGS. 1–3.
Figure 7B:
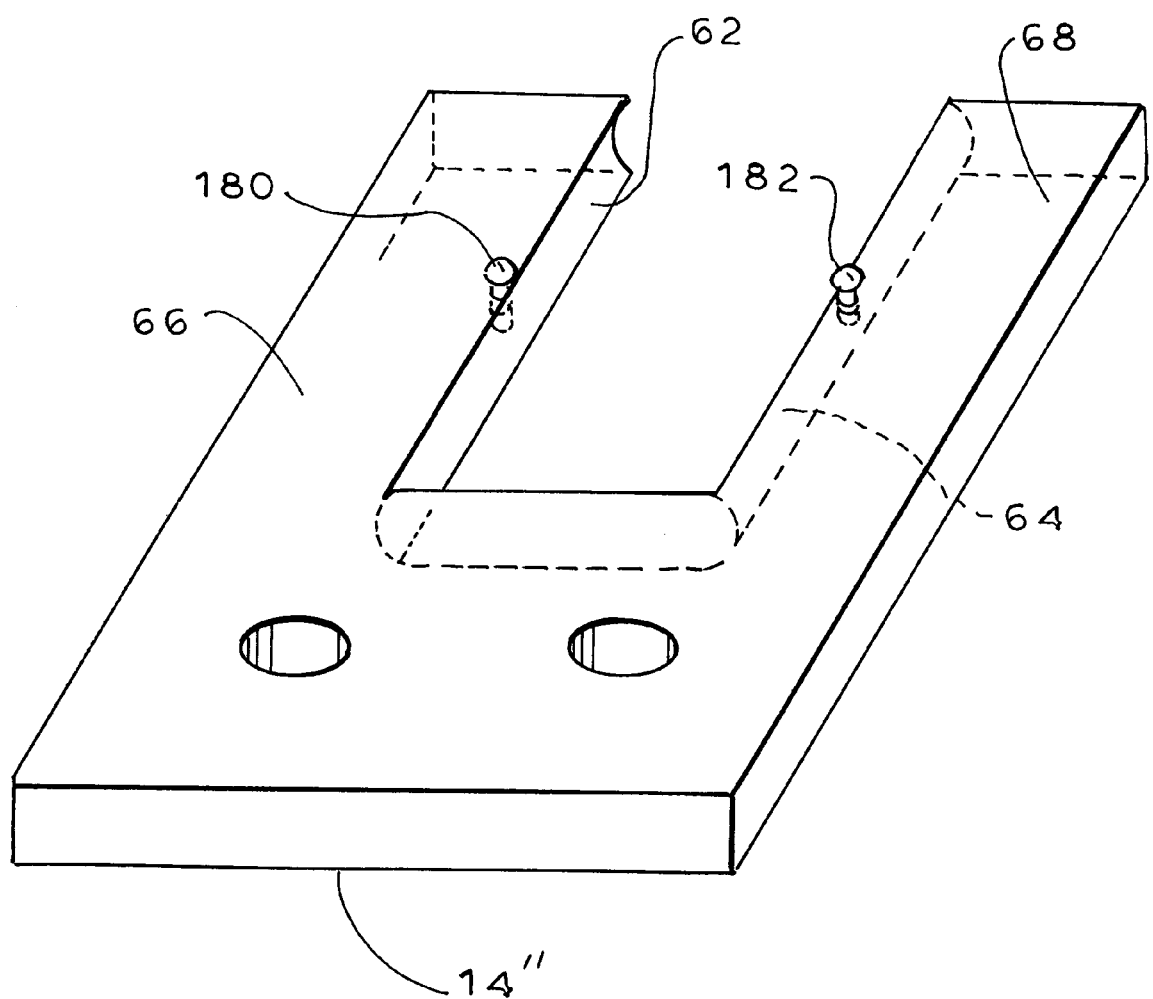
Figure 7C:
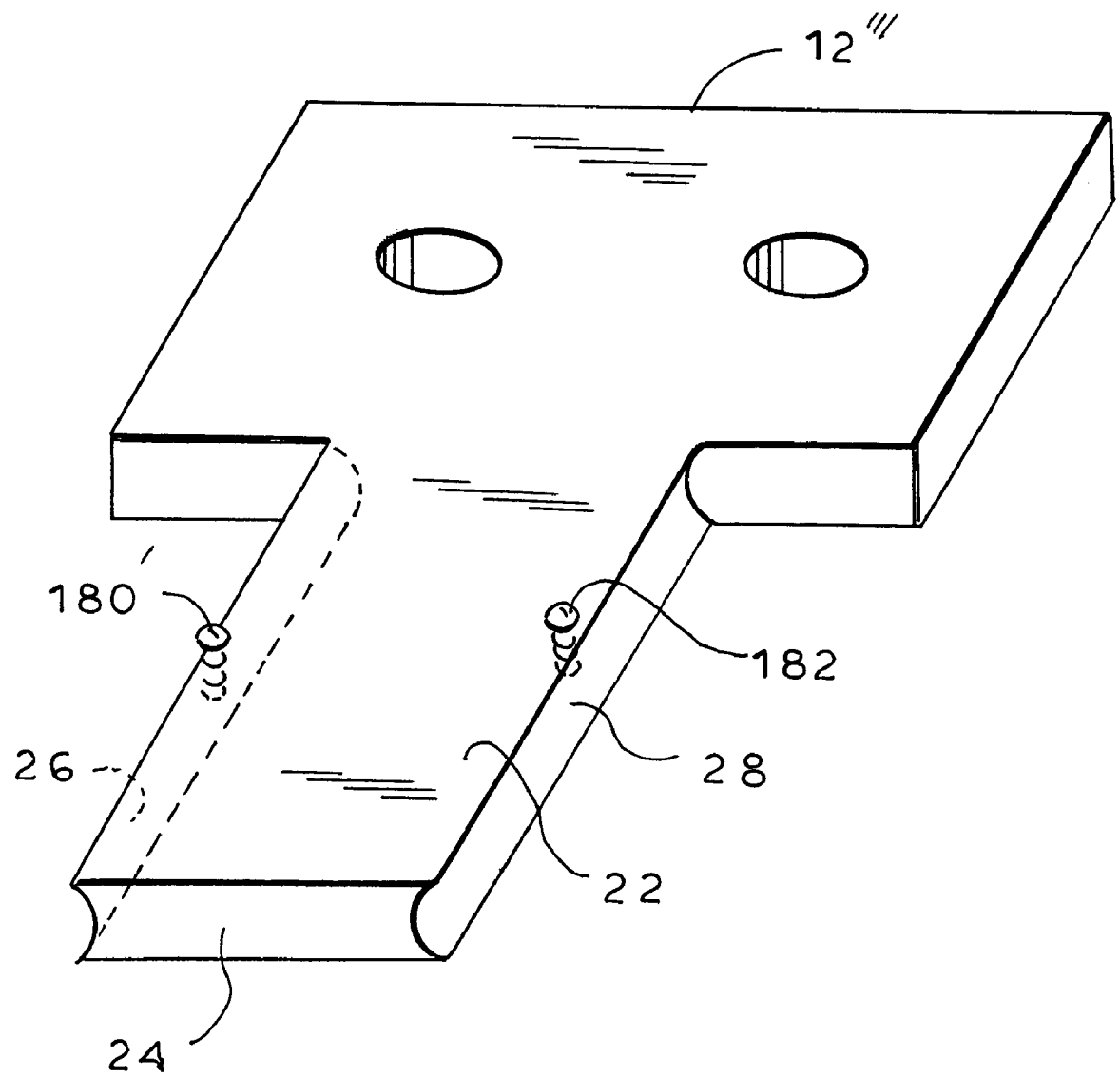
FIGS. 7c and 7d is a view of an additional alternative embodiments of plate 12 illustrated in FIGS. 1–6.
Figure 7D:
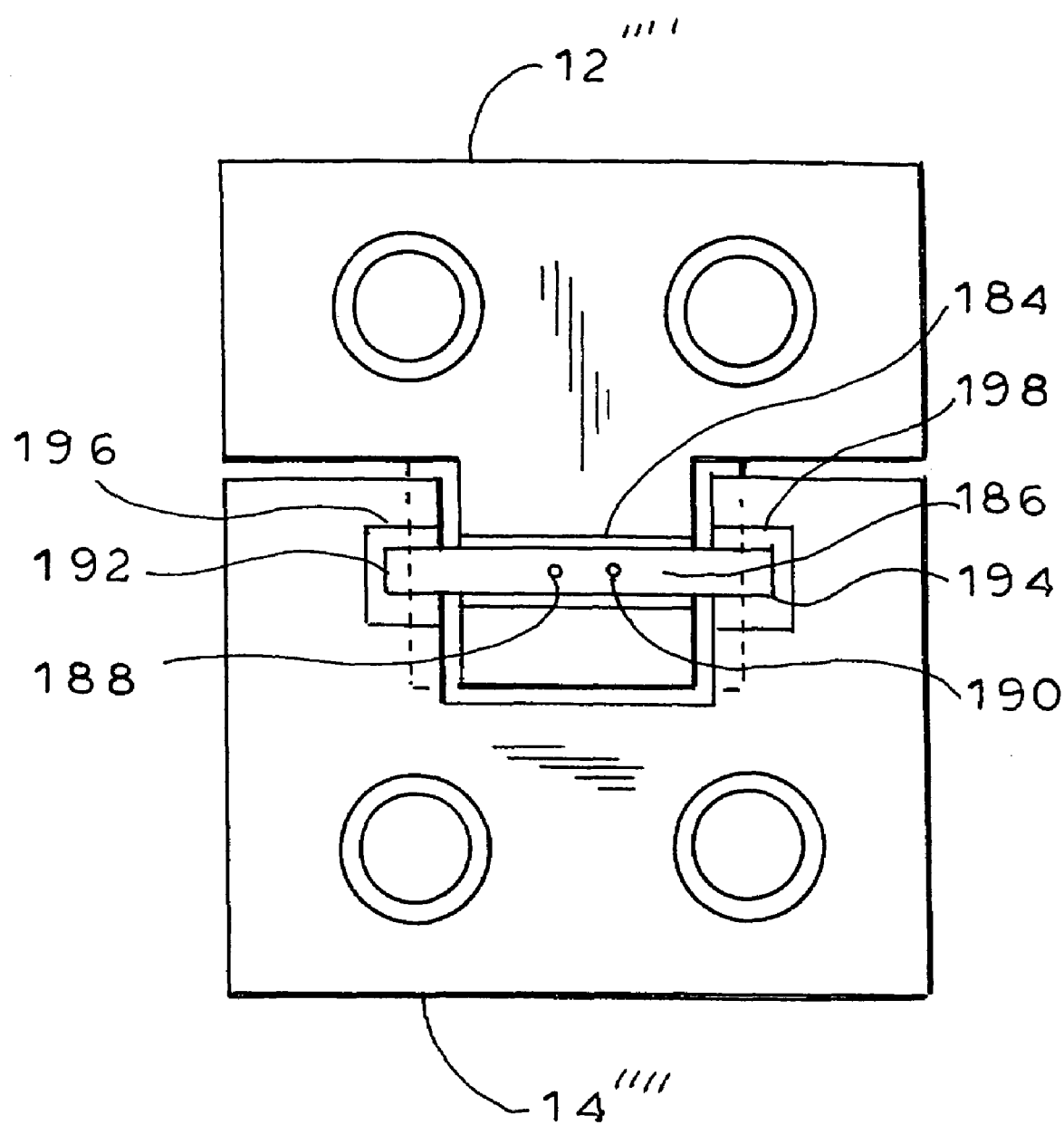
Figure 7E:
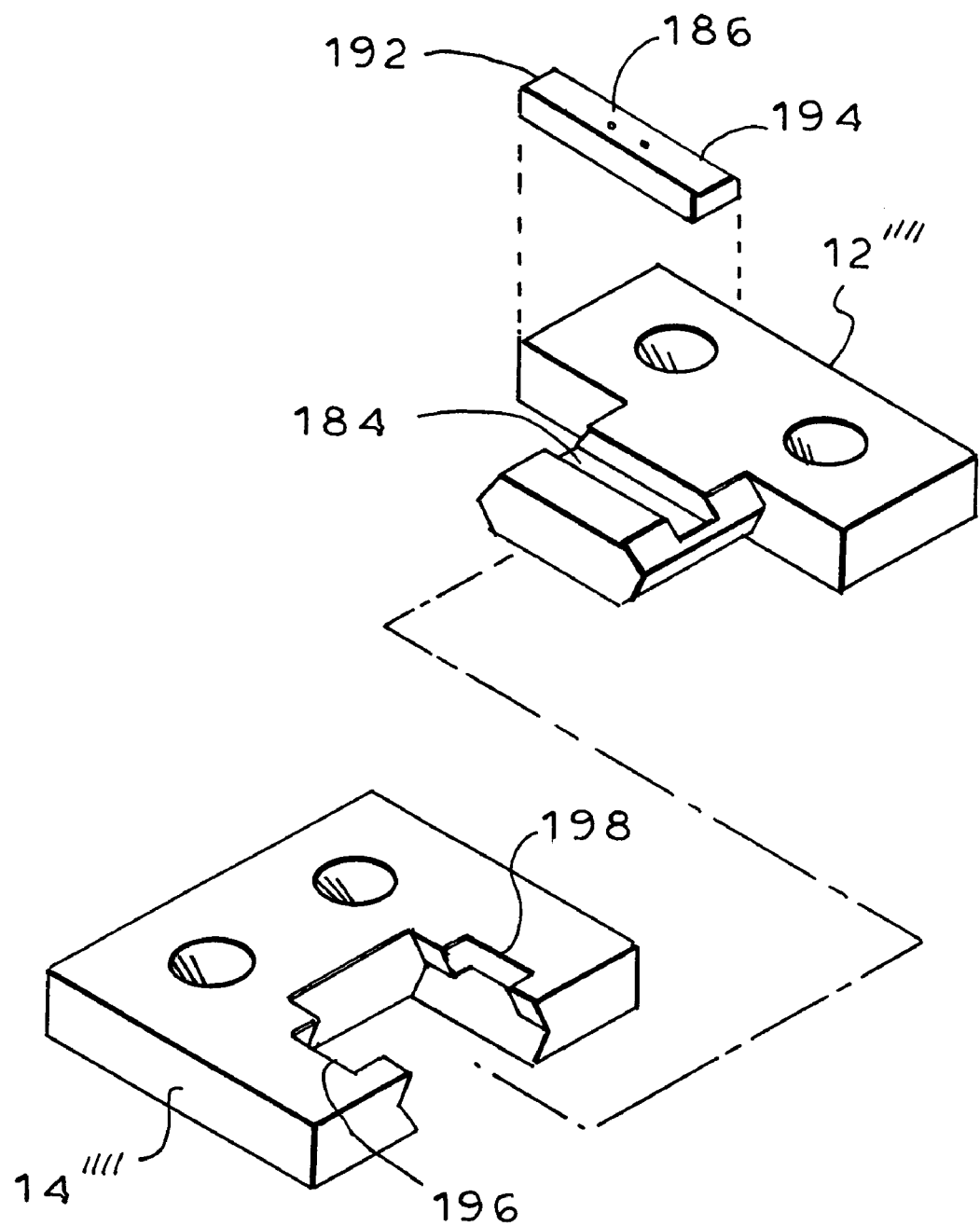
FIG. 7e are views of alternative embodiments of plates 12 and 14 illustrated in FIGS. 1–6.

The two sides 26, 28 of the first plate and the opposing inner edges 62, 64 of the side members 66, 68 of the second plate 14 are preferably designed to interconnect to prevent the two plates from rotationally separating. This is achieved in the preferred embodiment in FIGS. 1–4 by the sides of the tongue of the first plate 26, 28 having protuberances such that the center of the side 38 is wider than the top and bottom of the tongue 40 (FIG. 2). This allows the tongue to interconnect with the groove of the second plate 58, which has inner edges 62, 64 that form recesses complementary to the tongue protuberances, such that the center of the sides of the groove 82 is narrower than the top and bottom 84 (FIG. 2). FIG. 2a shows an alternate form of this embodiment. However, the apparatuses of these embodiments are not limited to the illustrated means for preventing rotational separation of the plates; any appropriate means for interconnecting the tongue and groove to prevent rotational separation of the plates can be utilized. For example, the sides of the tongue of the first plate can have recesses that interconnect with protuberances on the inner edges of the groove, as illustrated in FIG. 7c. In additional embodiments, the interconnection of the tongue of the first plate and the groove of the second plate is achieved by a wedge formed by the sides of the first plate matching an opposing wedge formed by the inner edges of the side members of the second plate.

Figure 4:
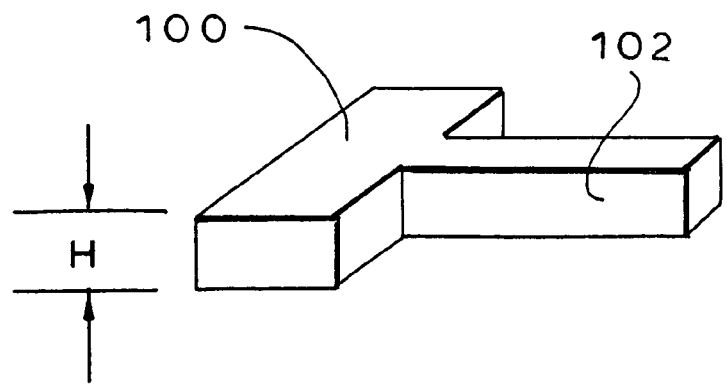
FIG. 4 is a view of one embodiment of the plate spacer of the apparatus of FIG. 1.

The space between the end of the tongue 24 and the top of the base of the groove 50 can accommodate a plate spacer 100 (exemplified in FIG. 4). The plate spacer 100 is used to separate the two plates axially while the plates are being affixed to the vertebrae. Optionally, more than one plate spacer can be placed between the two plates to achieve a greater separation than provided with one plate spacer. After the plates are affixed, the plate spacer is removed. In preferred embodiments, the plate spacer has a holder 102 that facilitates the removal of the plate spacer. As illustrated in FIG. 4, the plate spacer is a rectangular block and the holder is a tab protruding from the plate spacer. However, the plate spacer and the holder can take any appropriate shape. Additionally, the plate spacer can be placed anywhere that allows it to temporarily separate the two plates axially. For example, the plate spacer can be placed between the base of the first plate 20 and the tops of the sides of the groove 82, 84. All that is required is that the plate spacer be suitable for temporarily separating the two plates longitudinally until they are affixed to the vertebrae.

The plate spacer 100 has a height H that corresponds to the distance that the two plates 12, 14 are separated when the plate spacer is placed between them. The subsidence that can take place between the grafted vertebrae after the apparatus is implanted is equivalent to the height of the plate spacer. This height can be from 1 to 10 mm, preferably from 1 to 5 mm. The selection of the plate spacer height, or the number of plate spacers, for any particular situation is within the skill of the art without using undue experimentation.

In some instances, there may be a concern that the interconnecting plates, when implanted, could extend axially, during anatomic extensions, to such a degree that the plates become disengaged, with disastrous consequences. In those instances, the plates can comprise a means for limiting axial extension of the first plate with respect to the second plate. An example of such a means is illustrated in FIGS. 5–7. FIG. 5 illustrates plate 12', FIG. 6 illustrates plate 12", and FIG. 7c illustrates plate 12''' any of which would substitute for plate 12 of FIGS. 1–3. The three plates 12', 12" and 12''' completely correspond to plate 12 in each element except for the indentations 120 and 122 in the two sides of the tongue of the plate illustrated in FIG. 5, the indentations 124 and 126 in the two sides of the tongue of the plate illustrated in FIG. 6, and the setscrews 180' and 182' in the two sides of the tongue of the plate illustrated in FIG. 7c. The plate 12' or 12" function with the plate 14' of FIG. 7a or plate 14" of FIG. 7b to provide the means for limiting axial extension of the plates when they are interconnected. The plates 14' of FIG. 7a and 14" of FIG. 7b completely correspond to plate 14 illustrated in FIGS. 1–3 in each element except for the tabs 140 and 142 of the plate illustrated in FIG. 7a and the setscrews 180 and 182 of the plate illustrated in FIG. 7b. When the means for limiting axial extension is employed, the plate 14' or 14" is slidably interconnected along inner edges 62 and 64 with plate 12' or plate 12" along the edges 26 and 28 of the tongue 22 as with the previously described embodiments illustrated in FIGS. 1–3. The tabs 140 and 142 (FIG. 7a) or the setscrews 180 and 182 (FIG. 7b) protrude into the space in the tongue edges 26 and 28 created by the indentations 120 and 122 (FIG. 5) or 124 and 126 (FIG. 6) to prevent the two plates from extending axially to such an extent that the plates disengage.

The engagement of the tabs to limit axial extension proceeds as follows. When the plates are slidably interconnected, the tabs 140 and 142 or setscrews 180 and 182 are situated such that they do not interfere with the interconnection. After the plates are slidably interconnected, the tabs 140 and 142 or setscrews 180 and 182 are moved into the space created by the indentations 120 and 122 or 124 and 126. With the tabs 140 and 142 illustrated in FIG. 7a, the tabs are moved by bending the tabs into the space, for example with a pliers, hammer, crimping tool, or by any other means. In the embodiments employing tabs (e.g., FIG. 7a), the tabs must be made of a material that can be readily bent, as is know in the art. However, as envisioned herein, the means for limiting axial extension is not limited to bendable protrusions as illustrated in FIG. 7a or setscrews as illustrated in FIG. 7b, and can take any form known in the art to serve the purpose of limiting the axial extension of the two plates by protruding into the space created by the indentations 120 and 122 or 124 and 126. For example, the tabs can also be a separate piece of material that, after the plates are slidably interconnected, is screwed into a screwhole that has been predrilled into the side members 66, 68. With the setscrews 180 and 182 illustrated in FIG. 7b, the setscrews are screwed into the space, e.g., with a screwdriver.

In alternative preferred embodiments, the means for limiting axial extension of the two plates is provided by a bar spanning the width of the tongue and overlapping the sides of the groove. The bar can be affixed either to the tongue or the sides of the groove. One version of these embodiments is provided as FIGS. 7D and 7E. Tongue plate 12'''' has an indentation 184 that accommodates bar 186, which is affixed to tongue plate 12'''' by screws 188, 190 passing through screwholes in the bar and tongue. The ends of the bar 192, 194 overlap the sides of the groove in plate 14'''' in indentations 196, 198, which are wide enough to accommodate axial extension and compression of the tongue and grove plates with respect to each other as previously described.

Although the means for limiting axial extension of the two plates is illustrated in FIGS. 5–7 as comprising indentations in both sides of the tongue matching tabs or setscrews on both sides of the groove, or a bar crossing the tongue and overlapping the sides of the groove, the invention is not limited to those illustrated embodiments. For example, the means can be provided, for example, by tabs on the sides of the tongue matching indentations in the sides of the groove, or setscrews in the side of the tongue (FIG. 7c), where the sides of the tongue 26, 28 are concave, as with plate 12'''. The means for limiting axial extension can also be achieved with the tab/indentation or setscrew/indentation combination on only one side of the interconnection. Furthermore, .the means for limiting axial extension using a bar crossing the tongue and overlapping the sides of the groove can be achieved by: affixing the bar into an indentation in the sides of the groove and crossing the tongue in an indentation wide enough to accommodate axial extension or compression, or affixing a bar with protrubances at either end that extend into an indentation on in the edges of the groove, etc. The skilled artisan can also envision similar means for limiting axial extension which are encompassed within the present invention.

It should also be understood that the means for limiting axial extension can be engaged either by the end user (i.e., the surgeon) or at the point of manufacture, such that the entire apparatus is provided to the end user already assembled.

The preferred embodiments described above are not limited to a tongue and groove arrangement as exemplified in FIGS. 1–7. The first plate need only comprise integral means for slidable interconnecting with the second plate, where the sliding occurs parallel to the long axis of the spinal column, and where the integral means prevents rotational and transverse movement of the first vertebra relative to the second vertebra. The skilled artisan could readily devise configurations other than the tongue and groove arrangement exemplified in FIGS. 1–4. For example, the slidable interconnection of the two plates can be achieved with two tongues and grooves, or a tongue that is thinner than the second plate and that slips into a groove-shaped slot in the second plate.

Before implantation, the apparatus is sterilized by any appropriate means to prevent infection.

To implant the apparatus, the two plates 12, 14 are interconnected and attached to vertebrae with the plate spacer 100 in place. The plate spacer is then removed. The interconnection of the plates and attachment to the vertebrae can be achieved by any sequence of steps.

In a preferred embodiment, the first plate 12, the second plate 14, and the plate spacer(s) 100 are packaged together as a sterile assembly with removable fasteners that prevent the assembly from separating. If utilized, the means to prevent axial extension is also engaged. The assembly is aligned to the exposed anterior surface of the two grafted vertebrae. The first plate 12 and the second plate 14 are affixed to the vertebrae using screws 30, 32 and 74, 76 or other conventional fastening means, and the plate spacer 100 and fasteners are then removed.

In another preferred embodiment, the first plate 12 is first interconnected to the second plate 14, the plate spacer 100 is placed between the first plate and the second plate, the first plate-plate spacer-second plate assembly is aligned to the exposed anterior surface of the two grafted vertebrae, the first plate 12 and the second plate 14 are affixed to the vertebrae, and the plate spacer 100 is then removed and the means to limit axial extension is engaged, if utilized.

In an additional preferred embodiment, after a graft is placed between the two cervical vertebrae to be fused, the first plate 12 is positioned over the exposed anterior surface of the spinal column C such that the base is over vertebra V1, and the tongue of the first plate 22 protrudes in the direction of vertebra V2. The tongue of the first plate can optionally extend so far as to overlap the graft site and cover part of V2. Care must be taken to be sure that the second plate 14, when interconnected with the first plate 12, will be situated such that the holes 74, 76 are over an area of vertebra V2 suitable for inserting screws to affix the second plate 14 with vertebra V2.

With the first plate 22 on vertebra V1, a suitable drill guide and drill (not shown) are used to drill fastener openings in vertebra V1 at the site on the surface of vertebra V1 of holes 30 and 32. The screws 34 and 36 are then inserted through holes 30 and 32 to connect the first plate 22 with vertebra V1.

The second plate 14 is then interconnected to the first plate 12 by sliding the groove of the second plate 58 onto the tongue of the first plate 22, leaving a space between the end of the tongue of the first plate 24 and the top of the base of the second plate 50. The plate spacer is then placed in the space between the first and second plate and the groove of the second plate 58 is further slid onto the tongue of the first plate 22 until the end of the tongue of the first plate 24 and the top of the base of the second plate 50 are separated by the height of the plate spacer. The second plate 14 is then affixed to vertebra V2 using screws, as previously described with the first plate and vertebra V1.

The plate spacer 100 is then removed from the space between the first plate and the second plate, and the means to limit axial extension is engaged, if utilized. Thus, in operation, the first plate 12 is separated from the second plate 14 by the height of the plate spacer H. The graft is then subjected to subsidence limited to the distance defined by the height of the plate spacer H. Minimization of stress shielding is therefore achieved without concern for excessive subsidence, since the height of the plate spacer H limits the amount of subsidence on the graft.

In another preferred embodiment, using procedures analogous to those described above, the second plate 14 is first affixed to vertebra V2, the first plate 12 is then interconnected to the second plate 14, the plate spacer 100 is placed between the first plate 12 and the second plate 14, the first plate is affixed to vertebra V1, and the plate spacer is removed and the means to limit axial extension is engaged, if utilized.

The apparatuses and methods for utilizing them described above are not limited to use with any particular graft material. They may be used with, e.g., cancellous autografts, allografts or xenografts, or with any artificial or natural bone substitutes known in the art. The apparatuses and methods can also be used with any type of graft, including bone grafts and interbody spacers such as cages or boxes.

The apparatuses of the preferred embodiments described above are useful for promoting fusion of two vertebrae even without the plate spacer. When implanted with the interconnecting means engaged but with a space between the two plates, the apparatuses minimize stress shielding (albeit without protection from excessive subsidence) using a more compact design and fewer parts than prior art apparatuses, e.g., as provided in U.S. Pat. No. 5,843,082. The compact design is partially due to the utilization of a means for slidably interconnecting the plates that is integral with the plates. This is opposed to the apparatus provided in U.S. Pat. No. 5,843,082, where the means for slidably interconnecting the plates is provided by holes in the plates interconnecting with bars that are external and not integral with the plates.

The invention is also directed to apparatuses that can be more generally described than the embodiments described above. In these embodiments, the invention is directed to apparatuses for promoting fusion of a first vertebra and a second vertebra in a spinal column with a graft between the first vertebra and the second vertebra. The apparatus comprise a first member for attachment to the first vertebra and a second member for attachment to the second vertebra; means for attaching the apparatus to the first vertebra at the first member; means for attaching the apparatus to the second vertebra at the second member; means for preventing rotational and transverse movement of the first vertebra relative to the second vertebra; and a plate spacer comprising a height, the plate spacer capable of insertion into the apparatus between the first member and the second member, wherein the plate spacer can be removed from the apparatus after the apparatus is attached to both the first vertebra and the second vertebra. As in the previously described embodiments, the height of the plate spacer provides a subsidence between the two vertebrae upon removal of the plate spacer, said subsidence being equivalent to the height of the plate spacer.

Also as with the previously described apparatuses, these apparatuses are not limited to use with any particular vertebrae, although the preferred vertebrae are cervical vertebrae. Additionally, these devices are preferably attached to adjacent vertebrae, although they could be used to stabilize three or more vertebrae.

Applying the above generalized apparatus to the apparatus illustrated in FIGS. 1–4, the first member comprises a first plate having a first base capable of attachment to the first vertebra, the first plate also having a tongue protruding from the first base with an end distal to the first base and two sides perpendicular to the end; and the second member comprises a second plate having a second base, the second base having two sides and a top, wherein the second base is capable of attachment to the second vertebra, the second plate having a groove formed by a top of the second base and inner edges of side members protruding from the two sides of the second base.

As with previously described apparatuses, these apparatuses are useful in methods for promoting fusion of vertebrae. These methods comprise providing an apparatus, the apparatus comprising: means for attaching the apparatus to the first vertebra at the first member; means for attaching the apparatus to the second vertebra at the second member;

means for preventing rotational displacement of the first vertebra from the second vertebra; and a plate spacer capable of insertion into the apparatus between the first member and the second member, wherein the plate spacer can be removed from the apparatus after the apparatus is attached to both the first vertebra and the second vertebra. The apparatus is then attached to the first vertebra at the first member; the means for preventing rotational displacement of the first vertebra from the second vertebra is engaged; the plate spacer is placed between the first member and the second member; the first member is aligned to the second member at the plate spacer; the apparatus is attached to the second vertebra at the second member; and, finally, the plate spacer is removed from between the first member and the second member. As with other methods of the invention, the above order need not be followed in executing the method, except for the last step (removal of the plate spacer).

Also as with previously described methods; these methods can be used with any vertebrae, but cervical vertebrae are preferred; the methods can also be used to stabilize more than two vertebrae, although two adjacent vertebrae are preferred.

The invention is also directed to apparatuses for promoting fusion of more than two vertebrae, using plates mountable to each vertebrae. As with the previously described apparatuses, each plate comprises integral means for slidably interconnecting with adjacent plate(s), where the sliding occurs parallel to the long axis of the spinal column, and where the integral means prevents rotational and transverse movement of the vertebrae to which the plates are mounted. Also as with the previous embodiments, the vertebrae are preferably cervical vertebrae. The plates can be fastened to the vertebrae by any means known in the art, for example with screws that pass through holes in the plates and screw into the vertebrae. The apparatuses of these embodiments also preferably include a removable plate spacer mounted between each two adjacent plates. The plate spacer is removed after the apparatus is implanted, to allow subsidence at the graft to take plate that is equivalent to the height of the plate spacer. Also as with previously described embodiments, the apparatus optionally includes a means for limiting axial extension of each two adjacent plates relative to each other. These apparatuses also should be sterilized before implantation.

Figure 8A:
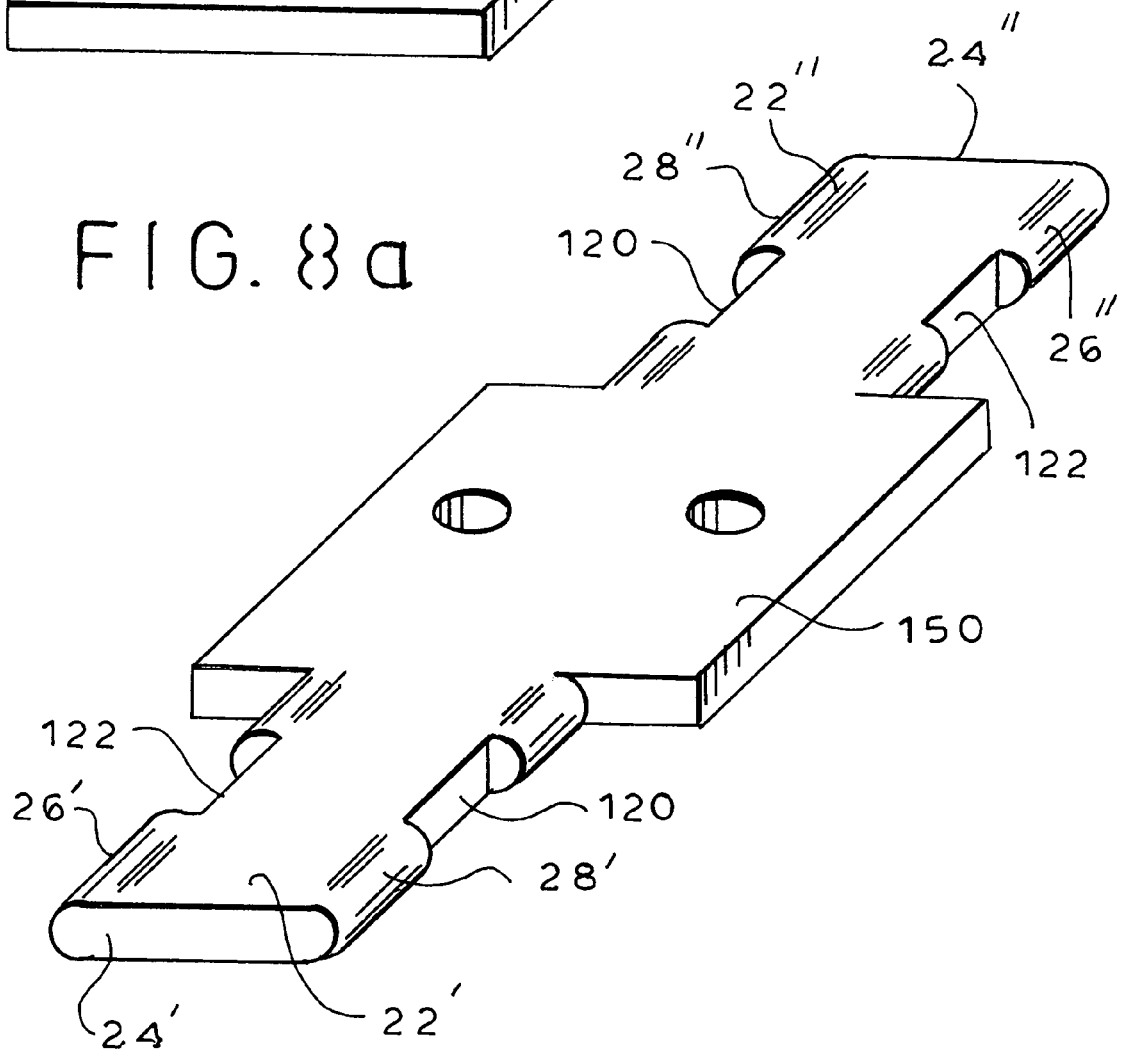

In some preferred embodiments, these apparatuses utilize plates where the means for slidably interconnecting the plates are interconnecting tongue and groove elements, as with previously described tongue and groove elements. In these embodiments, the plates mountable to the vertebrae on the ends (i.e., the first and the third vertebrae if three vertebrae are being fused; or the first and the fourth vertebrae if four vertebrae are being fused, etc.) are identical to the plates previously described and illustrated in FIGS. 1–7. The plate on either end can be either the tongue plate (e.g., FIGS. 5 or 6) or the groove plate (e.g., FIGS. 7a or 7b). The plate(s) mountable to the vertebra(e) that are not on the ends (i.e., the second vertebra if three vertebrae are being fused, or the second and third vertebrae if four vertebrae are being fused, etc.) have a combination of two tongues, a tongue and a groove, or two grooves, as appropriate to have a slidably interconnecting tongue and groove between each two adjacent plates. An example of each of the three possible internal plates for these embodiments is illustrated in FIG. 8*a* (two tongues), FIG. 8*b* (a tongue and a groove), and FIG. 8*c* (two grooves). The elements of these internal plates are completely analogous in materials, construction, and structure to the plates previously described and illustrated in FIGS. 1–7.

Thus, the plate illustrated in FIG. 8*a* has a base 150 mountable to a vertebra, with a first tongue 22' protruding from the base 150 with an end 24' distal to the base 150 and two sides 26', 28' perpendicular to the end 24'. The plate also has a second tongue 22" protruding from the base 150 with an end 24" distal to the base 150 and two sides 26", 28" perpendicular to the end. The first tongue 22' and the second tongue 22" are directed in opposite directions along the long axis of the spinal column.

The plate illustrated in FIG. 8*b* has a base 160 mountable to a vertebra, with a tongue 22' protruding from the base 160 with an end 24' distal to the base 160 and two sides 26', 28' perpendicular to the end 24'. The plate also has a groove 58' formed by an edge 60' at the top of the base 160 and inner edges 62', 64' of the two sides 66', 68' of the base. The tongue 22' and the groove 58' are directed in opposite directions along the long axis of the spinal column.

The plate illustrated in FIG. 8*c* has a base 170 mountable to a vertebra, with two sides 66', 68', a top 172 and a bottom 174. The plate also has a first groove 58' formed by the top 172 of the base 170 and inner edges 62', 64' of the two sides 66', 68' of the base 170. Additionally, the plate has a second groove 58" formed by the bottom 174 of the base 170 and inner edges 62", 64" of the two sides 66", 68" of the base. The first groove 58' and the second groove 58" are directed in opposite directions along the long axis of the spinal column.

Figure 9A:
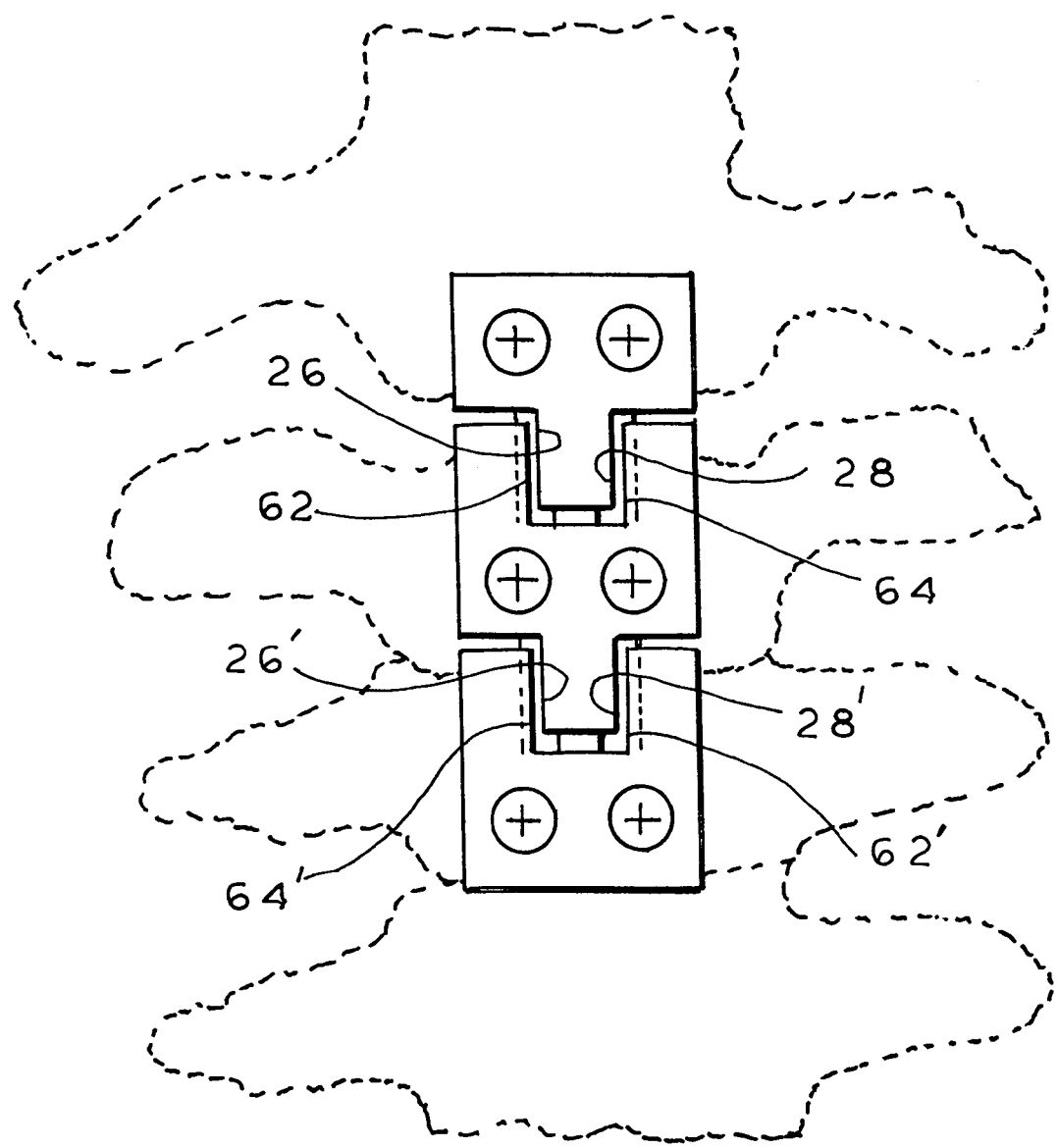
FIGS. 9a, 9b and 9c are elevational views of three apparatuses constructed in accordance with the present invention for stabilizing three vertebrae, as seen before removal of the plate spacers, the apparatuses variously using the plates illustrated in FIGS. 5–8.
Figure 9B:
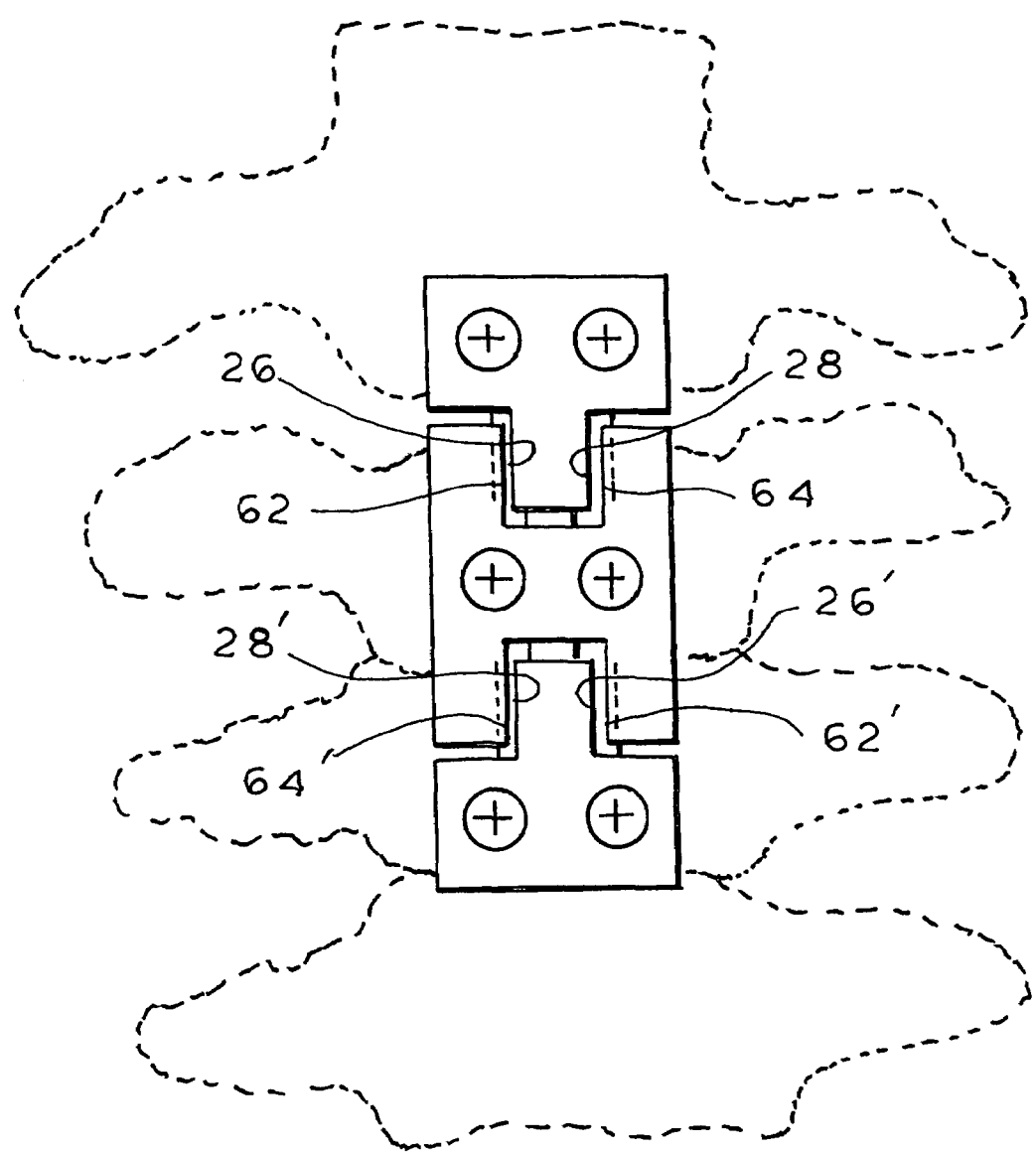
Figure 9C:
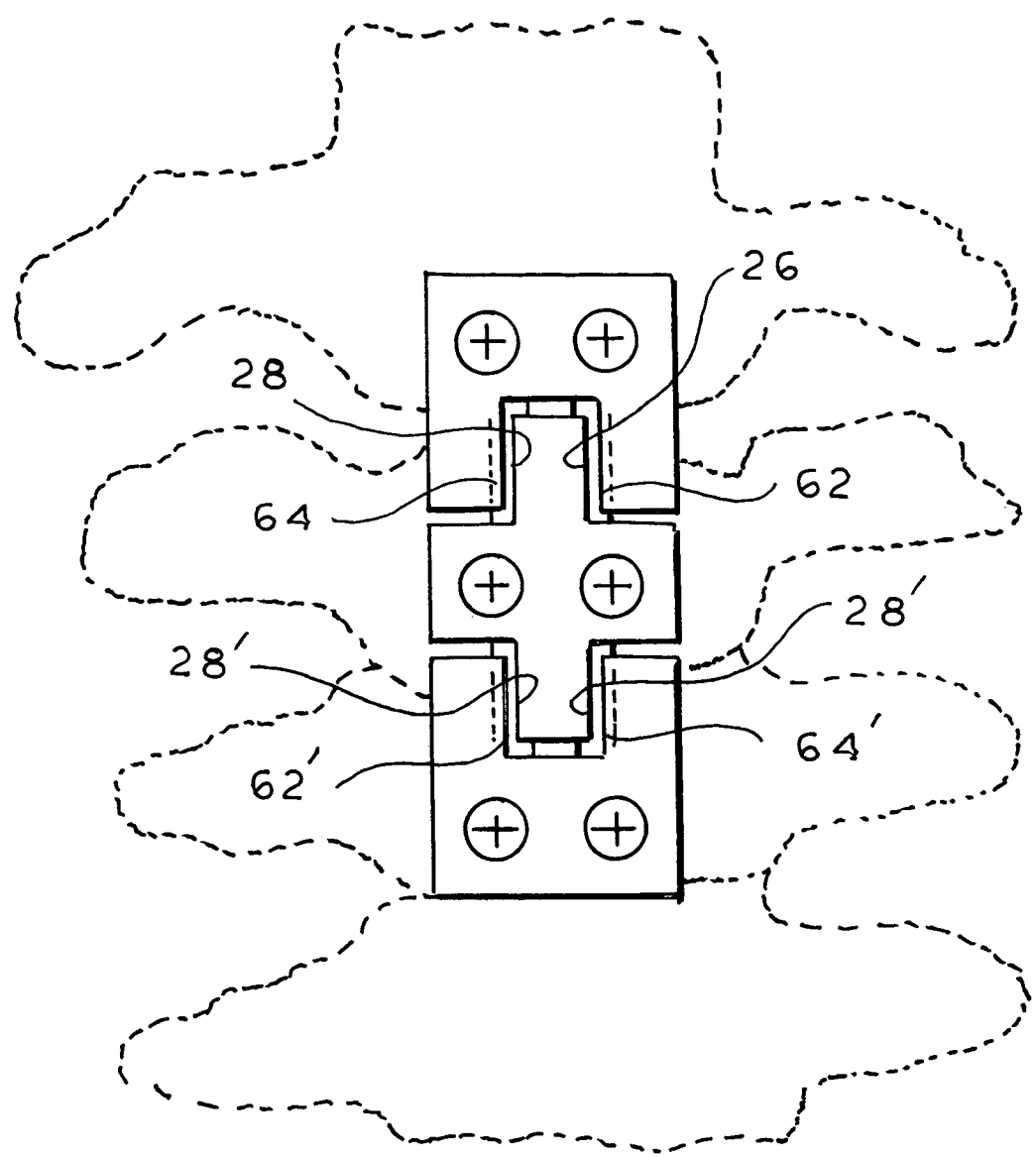

When one of the three plates illustrated in FIGS. 8*a*–8*c* is utilized with two of any of the previously described plates (e.g., as illustrated in FIGS. 1–7) on three fused vertebrae, they are implanted onto the vertebrae as illustrated in FIG. 9*a*, 9*b* or 9*c*. In those figures, the first plate and the second plate slidably interconnect when attached to the first and second vertebrae. The interconnection occurs at (a) the two sides 26, 28 or 26', 28' of the tongue of one of the first plate or the second plate and (b) the inner edges 62, 64 or 62', 64' of the two sides of the groove on the other of the first plate or the second plate. Also, the second plate and the third plate slidably interconnect when attached to the second and third vertebrae. The interconnection occurs at (a) the two sides 26, 28 or 26', 28' or 26", 28" of the tongue of one of either the second plate or the third plate and (b) the inner edges 62, 64 or 62', 64' or 62", 64" of the two sides of the groove on the other of the second plate or the third plate. Combinations of these plates other than those illustrated in FIGS. 9A, 9B and 9C are possible, for example the same interconnecting combinations as shown in FIG. 9 can be utilized where the assembly is turned upside down in relation to the vertebrae.

When two of the three plates illustrated in FIG. 8 is utilized with two of any of the previously described plates (e.g., as illustrated in FIGS. 1–7) on four fused vertebrae, they are implanted onto the vertebrae as illustrated in FIG. 10*a*, 10*b*, 10*c*, or 10*d*. In those figures, the first plate and the second plate slidably interconnect when attached to the first and second vertebrae. The interconnection occurs at (a) the two sides 26, 28 or 26', 28' of the tongue of one of the first plate or the second plate and (b) the inner edges 62, 64 or 62', 64' of the two sides of the groove on the other of the first plate or the second plate. Also, the second plate and the third plate slidably interconnect when attached to the second and third vertebrae. The interconnection occurs at (a) the two sides 26, 28 or 26', 28' or 26", 28" of the tongue of one of either the second plate or the third plate and (b) the inner edges 62, 64 or 62', 64' or 62", 64" of the two sides of the groove on the other of the second plate or the third plate. Additionally, the third plate and the fourth plate slidably interconnect when attached to the third and fourth vertebrae.

Figure 10A:
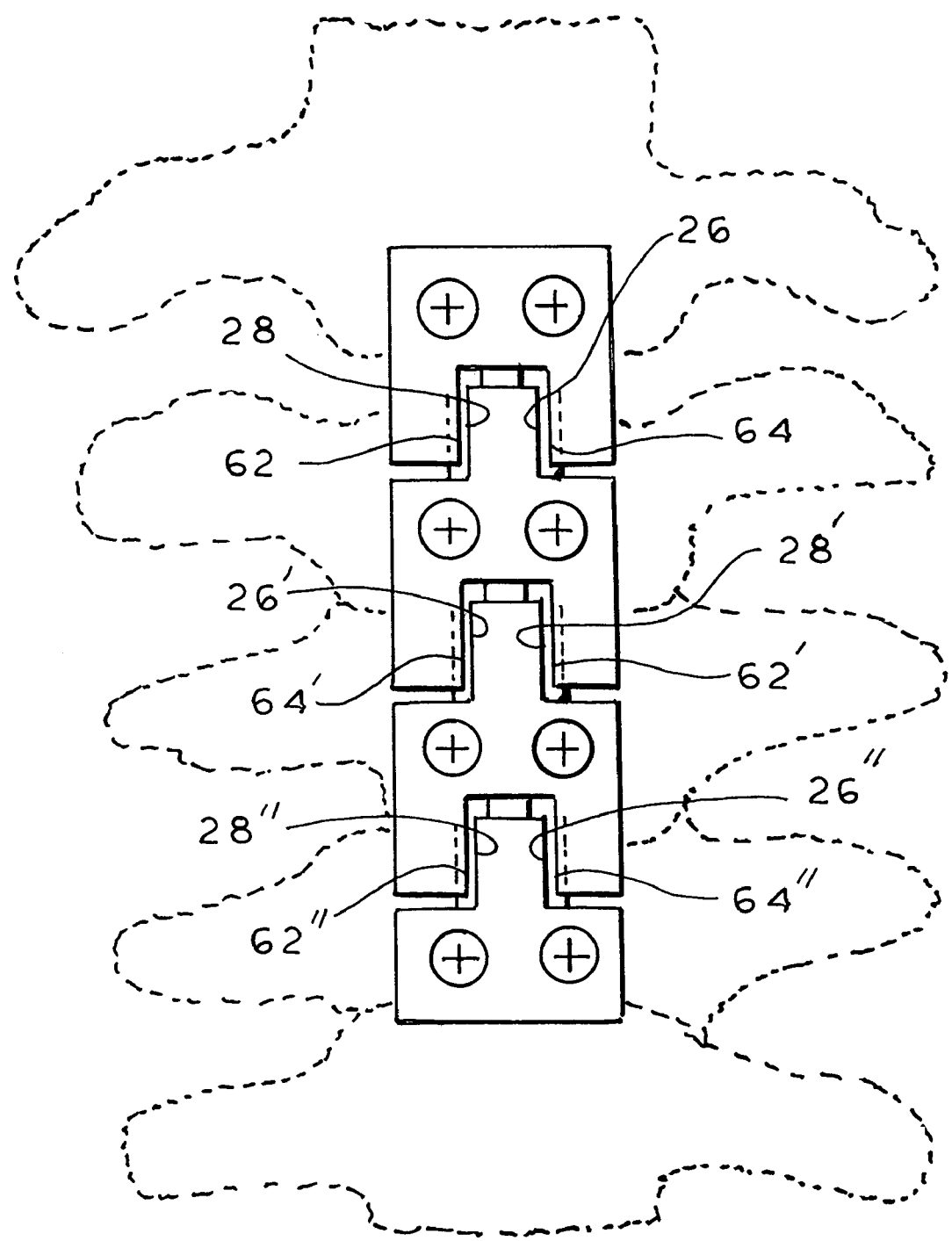
FIGS. 10a, 10b, 10c and 10d are elevational views of four apparatuses constructed in accordance with the present invention for stabilizing four vertebrae, as seen before removal of the plate spacers, the apparatuses variously using the plates illustrated in FIGS. 5–8.
Figure 10:
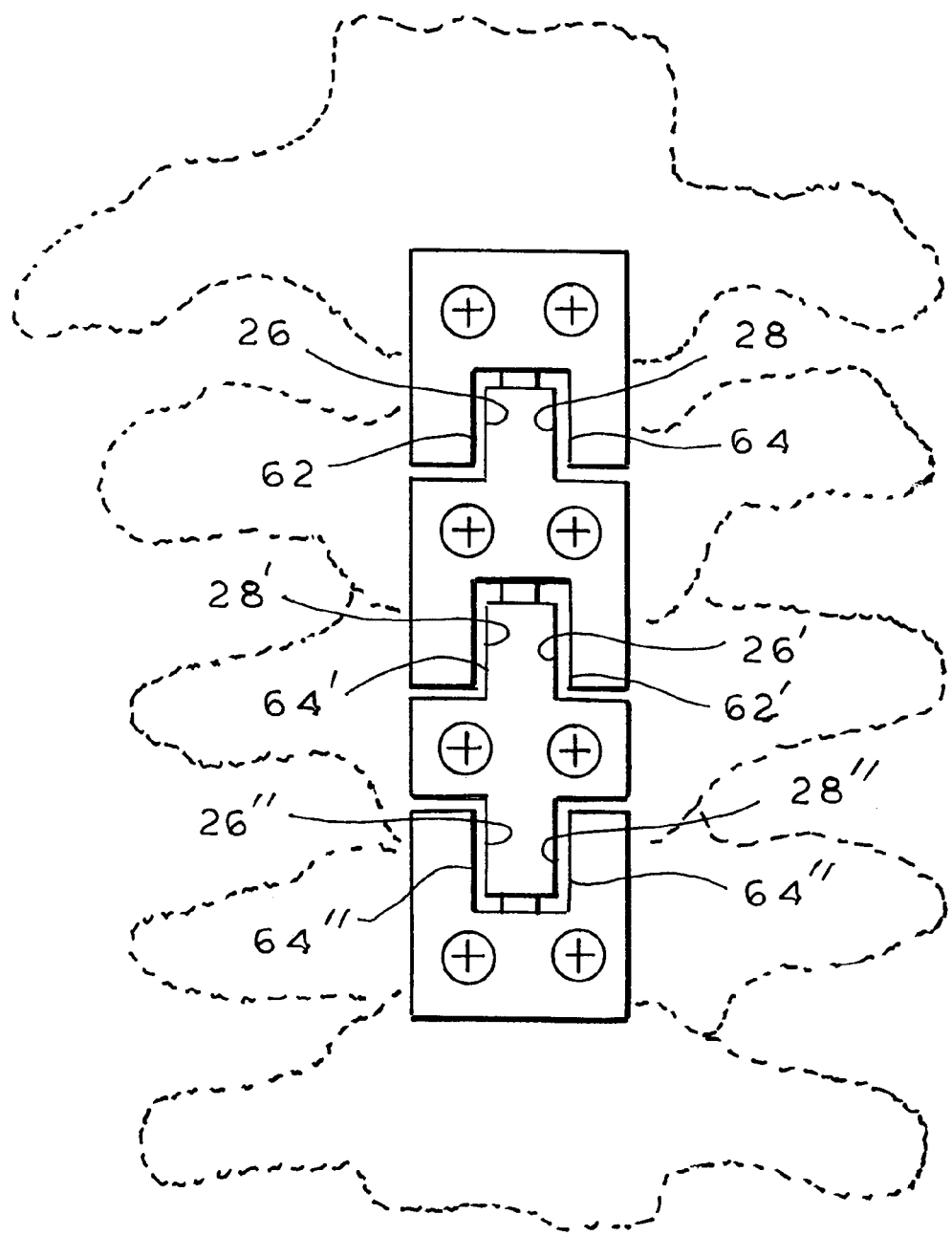
Figure 10C:
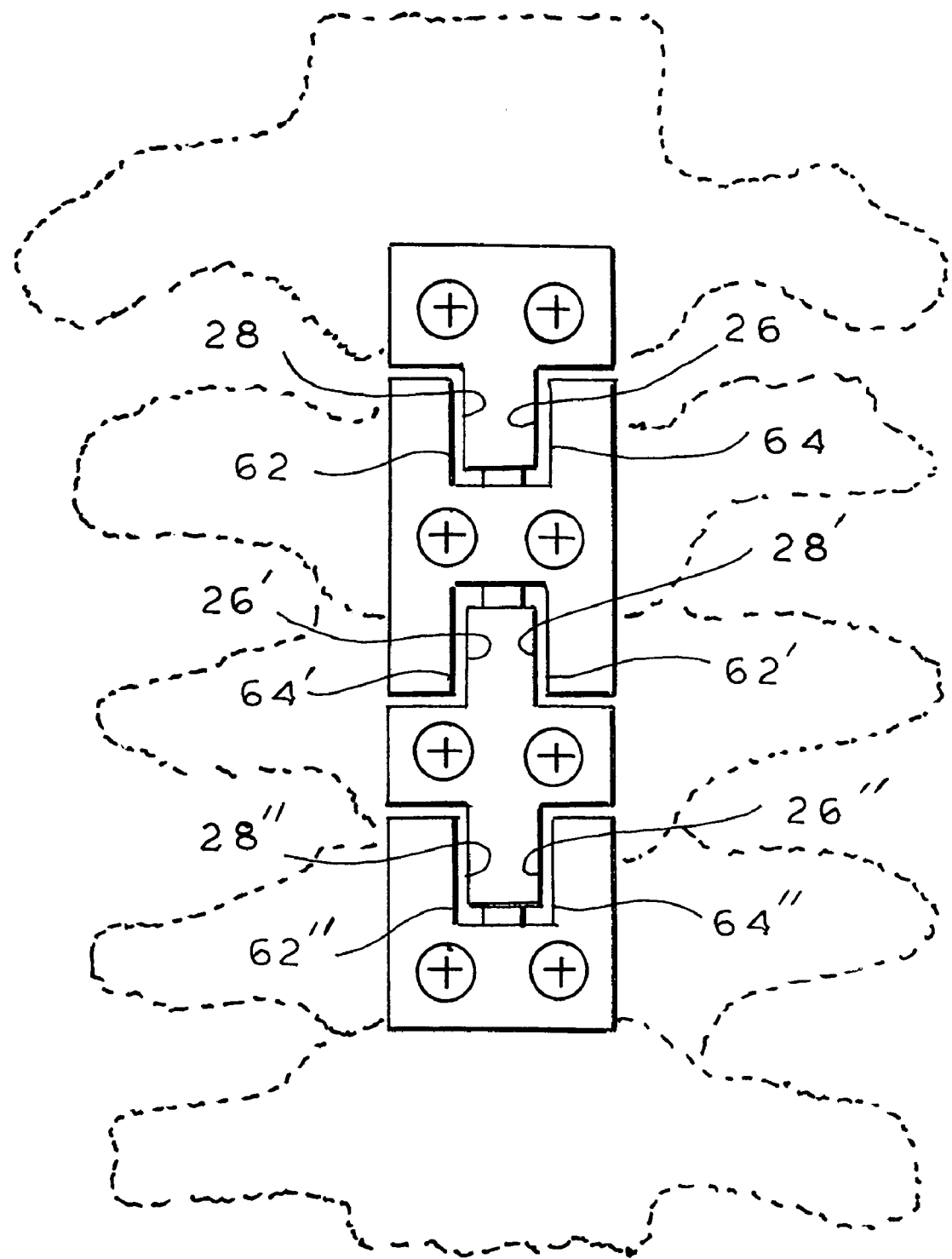
Figure 10D:
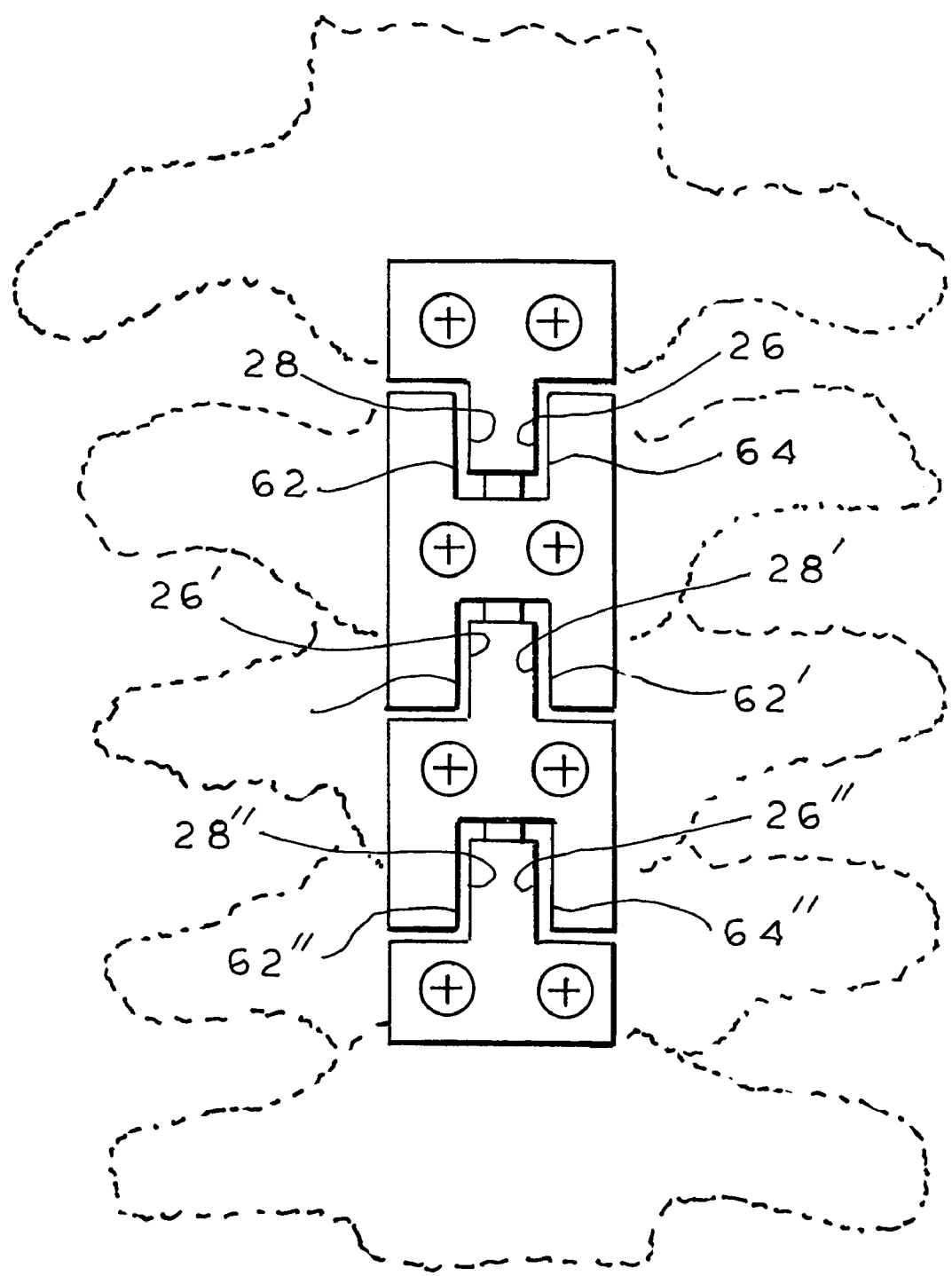

The interconnection occurs at (a) the two sides 26, 28 or 26', 28' or 26", 28" of the tongue of one of either the third plate or the fourth plate and (b) the inner edges 62, 64 or 62', 64' or 62", 64" of the two sides of the groove on the other of the third plate or the fourth plate. Combinations of these plates other than those illustrated in FIGS. 10a, 10b, 10c and 10d are possible, for example the same interconnecting combinations as shown in FIG. 10 can be utilized where the assembly is turned upside down in relation to the vertebrae.

Generalizing this system with n number of adjacent vertebrae having n-1 number of fusions between the n vertebrae, these embodiments encompass apparatuses for promoting fusion of n adjacent vertebrae in a spinal column at grafts between each of the n vertebrae. The n vertebrae comprise a first vertebra, an nth vertebra, and n-2 vertebra(e) between the first vertebra and the nth vertebra. The apparatuses comprise n plates, where each plate is mountable to one of each of the n vertebrae. Each plate comprises integral means for slidably interconnecting with adjacent plate(s). The sliding occurs parallel to the long axis of the spinal column. The integral means prevents rotational and transverse movement of the each of the n vertebrae relative to each adjacent vertebra(e) of the n vertebra. Preferably, there are also n-1 removable plate spacers, each plate spacer mounted between each two adjacent interconnecting plates.

These embodiments encompass the fusion of two, three, four, five or more vertebrae as exemplified using the apparatuses previously described, and illustrated for example in FIGS. 1–10. Where only two vertebrae are fused, n=2. Of course, there are no vertebrae between the first vertebra and the second vertebra (n-2=0).

These embodiments can also be used to fuse nonadjacent vertebrae together with an interbody graft in place of the intervening vertebra(e) that has been resected by a surgical procedure, generally known as vertebrectomy or corpectomy. In these scenarios, one, two or more vertebrae are removed or resected and replaced by an interbody spacer known in the art, such as a long graft or cage.

Where these embodiments utilize the plates exemplified in FIGS. 1–10, the plate mountable to the first vertebra and the plate mountable to the nth vertebra is independently selected from the two plates illustrated in FIGS. 1–7. These can be described as (1) a plate with a base 20 mountable to the vertebra, the plate also having a tongue 22 protruding from the base 20 with an end 24 distal to the base 20 and two sides 26, 28 perpendicular to the end 24; and (2) a plate with a base 50 mountable to the vertebra, the base having two sides 66, 68 and a top, the plate having a groove 58 formed by a top of the base and inner edges 62, 64 of the two sides 66, 68 of the base 50. The plate mountable to each of the n-2 vertebra(e) between the first and the nth vertebrae is independently selected from the three plates illustrated in FIG. 8. They can be described as (i) a plate with a base 150 mountable to a vertebra, with a first tongue 22' protruding from the base 150 with an end 24' distal to the base 150 and two sides 26', 28' perpendicular to the end 24', the plate also having a second tongue 22" protruding from the base 150 with an end 24" distal to the base 150 and two sides 26", 28" perpendicular to the end, wherein the first tongue 22' and the second tongue 22" are directed in opposite directions along the long axis of the spinal column; (ii) a plate with a base 160 mountable to a vertebra, with a tongue 22' protruding from the base 160 with an end 24' distal to the base 160 and two sides 26', 28' perpendicular to the end 24', the plate also having a groove 58' formed by an edge 60' at the top of the base 160 and inner edges 62', 64' of the two sides 66', 68' of the base, wherein the tongue 22' and the groove 58' are directed in opposite directions along the long axis of the spinal column; and (iii) a plate with a base 170 mountable to a vertebra, with two sides 66', 68', a top 172 and a bottom 174, the plate having a first groove 58' formed by the top 172 of the base 170 and inner edges 62', 64' of the two sides 66', 68' of the base 170, the plate also having a second groove 58" formed by the bottom 174 of the base 170 and inner edges 62", 64" of the two sides 66", 68" of the base, wherein the first groove 58' and the second groove 58" are directed in opposite directions along the long axis of the spinal column. Each plate in the apparatus must also slidably interconnect with the adjacent plate(s) when attached to the vertebrae. The interconnection in these embodiments occurs at (a) the two sides 26, 28 or 26', 28' or 26", 28" of the tongue of one of the interconnecting plates, and (b) the inner edges 62, 64 or 62', 64' or 62", 64" of the two sides of the groove other of the interconnecting plates.

As with the analogous embodiments with two plates, these apparatuses can optionally comprise a means for limiting axial extension of two adjacent plates in relation to each other. For example, as illustrated in FIGS. 8a, 8b and 8c, at least one of the two sides of each tongue can comprise an indentation 120 or 122, and at least one of the inner edges 62', 64' or 62", 64" of the two sides of each groove can comprise a tab 140 or 142 or a setscrew (like 180 or 182 of FIG. 7b), where each tab 140 or 142 or setscrew of each groove is engagable into the indentation of a tongue such that the engagement of the tab 140 or 142 or setscrew limits axial extension of the first plate with respect to the second plate and the second plate with respect to the third plate when the plates slidably interconnect. Alternatively, at least one of the two sides of each tongue can comprise a tab or a setscrew (like 180' or 182' of FIG. 7c) and at least one of the inner edges of the two sides of each groove can comprise an indentation, where each tab or setscrew of each tongue is engagable into the indentation of a groove such that the engagement of the tab or setscrew limits axial extension of the first plate with respect to the second plate and the second plate with respect to the third plate when the plates slidably interconnect. The means for limiting axial extension can also be provided in these embodiments by using a bar crossing the tongue and overlapping the sides of the groove, as previously described.

In related embodiments, the invention is directed to methods for promoting fusion of more than one adjacent vertebrae in a spinal column at grafts between each adjacent two vertebrae. The method comprises mounting any of the apparatuses which include plate spacers, as described for this purpose above, to the vertebrae, then removing the plate spacers.

The present invention also encompasses any of the novel plates used in the apparatuses and methods described above.

Other embodiments within the scope of the claims herein will be apparent to one skilled in the art from consideration of the specification or practice of the invention as disclosed herein. It is intended that the specification be considered exemplary only, with the scope and spirit of the invention being indicated by the following claims.

In view of the above, it will be seen that the several advantages of the invention are achieved and other advantages attained.

As various changes could be made in the above methods and compositions without departing from the scope of the invention, it is intended that all matter contained in the above description and shown in the accompanying drawings shall be interpreted as illustrative and not in a limiting sense.

All references cited in this specification are hereby incorporated by reference. The discussion of the references herein is intended merely to summarize the assertions made by the authors and no admission is made that any reference constitutes prior art. Applicants reserve the right to challenge the accuracy and pertinence of the cited references.

What is claimed is:

1. An apparatus for promoting fusion of a first vertebra and a second vertebra in a spinal column at a graft between the first vertebra and the second vertebra, where the first vertebra and second vertebra are along a long axis forming the spinal column, the apparatus comprising
   a first plate mountable to the first vertebra comprising at least two edges parallel to the long axis of the vertebrae, and
   a second plate mountable to the second vertebra comprising at least two edges parallel to the long axis of the vertebrae,
   wherein the first plate comprises integral means for slidably interconnecting with the second plate at said edges of each plate that are parallel to the long axis of the vertebrae, said sliding occurring parallel to the long axis of the spinal column, said means preventing rotational movement of the first vertebra relative to the second vertebra,
   and wherein the plates can overlap only at the integral means for slidably interconnecting at said edges of each plate when the plates are slidably interconnected.

2. The apparatus of claim 1, wherein the first and second vertebrae are cervical vertebrae.

3. The apparatus of claim 1, wherein the first vertebra is adjacent to the second vertebra in the spinal column.

4. The apparatus of claim 1, wherein the first plate and the second plate each further comprise holes passing through the plate, and fastening means capable of passing through the holes for attaching the plate to the vertebra.

5. The apparatus of claim 1, further comprising a removable plate spacer mounted between the first plate and the second plate, said plate spacer comprising a height.

6. The apparatus of claim 5, wherein the plate spacer further comprises a holder and the height of the plate spacer is between about 1 mm and 5 mm.

7. The apparatus of claim 5, wherein the height of the plate spacer provides a subsidence between the two vertebrae upon removal of the plate spacer, said subsidence being equivalent to the height of the plate spacer.

8. The apparatus of claim 1, wherein
   the first plate has a first base mountable to the first vertebra, the first plate also having a tongue protruding from the first base with an end distal to the first base and two sides perpendicular to the end, and
   the second plate has a second base, the second base having two sides and a top, wherein the second base is capable of attachment to the second vertebra, the second plate having a groove formed by a top of the second base and inner edges of the two sides of the second base,
   wherein the tongue of the first plate and the groove of the second plate slidably interconnect when attached to the first and second vertebrae, the interconnection occurring at the two sides of the tongue of the first plate and the inner edges of the two sides of the second plate, and
   wherein the end of the tongue and the top of the second base are capable of touching, preventing compression of the first vertebra with the second vertebra.

9. The apparatus of claim 8, further comprising a removable plate spacer suitable for placing between the first plate and the second plate, said plate spacer comprising a height.

10. The apparatus of claim 9, wherein the plate spacer fits between the end of the tongue and the top of the second base.

11. The apparatus of claim 9, wherein the plate spacer further comprises a holder and the height of the plate spacer is between about 1 mm and 5 mm.

12. The apparatus of claim 9, wherein the height of the plate spacer provides a subsidence between the two vertebrae upon removal of the plate spacer, said subsidence being equivalent to the height of the plate spacer.

13. An apparatus for promoting fusion of a first vertebra and a second vertebra in a spinal column with a graft between the first vertebra and the second vertebra, where the first vertebra and second vertebra are along a long axis forming the spinal column, the apparatus comprising
   a first member for attachment to the first vertebra and a second member for attachment to the second vertebra, the first member and the second member each comprising at least two edges parallel to the long axis of the vertebrae;
   means for attaching the apparatus to the first vertebra at the first member;
   means for attaching the apparatus to the second vertebra at the second member;
   means in the first and second member for preventing rotational movement of the first vertebra relative to the second vertebra, wherein the means for preventing rotational movement is at said edges of each member that are parallel to the long axis of the vertebrae;
   a plate spacer comprising a height, the plate spacer capable of insertion into the apparatus between the first member and the second member, wherein the plate spacer can be removed from the apparatus after the apparatus is attached to both the first vertebra and the second vertebra,
   wherein the members can overlap only at the means for preventing rotational movement at said edges of each member when the apparatus is attached to the vertebrae, and
   wherein the height of the plate spacer provides a subsidence between the two vertebrae upon removal of the plate spacer, said subsidence being equivalent to the height of the plate spacer.

14. An apparatus for promoting fusion of n adjacent vertebrae in a spinal column at grafts between each of the n vertebrae, where the n adjacent vertebrae are along a long axis forming the spinal column, the apparatus comprising
   n plates, each plate comprising at least two edges parallel to the long axis of the vertebrae, and each plate mountable to one of each of the n vertebrae,
   wherein each plate comprises integral means for slidably interconnecting with adjacent plate(s) at said edges of each plate that are parallel to the long axis of the vertebrae, said sliding occurring parallel to the long axis of the spinal column, said means preventing rotational movement of the each of the n vertebrae relative to each adjacent vertebra(e) of the n vertebra,
   and wherein the plates can overlap only at the integral means for slidably interconnecting at said edges of each plate when the plates are slidably interconnected.

15. The apparatus of claim 14,
   wherein the n vertebrae comprise a first vertebra, an nth vertebra, and n−2vertebra(e) between the first vertebra and the nth vertebra, wherein the plate mountable to the first vertebra and the plate mountable to the nth vertebra are independently selected from the group consisting of a plate with a base mountable to the vertebra, the plate also having a tongue protruding from the base with an end distal to the base and two sides perpendicular to the end; and a plate with a base mountable to the vertebra, the base having two sides and a top, the plate having a groove formed by a top of the base and inner edges of the two sides of the base;

wherein the plate mountable to each of the n−2 vertebra(e) are independently selected from the group consisting of a plate with a base mountable to the vertebra, the plate also having a first tongue protruding from the base with an end distal to the base and two sides perpendicular to the end, the plate also having a second tongue protruding from the base with an end distal to the base and two sides perpendicular to the end, wherein the first tongue and the second tongue are directed in opposite directions along the long axis of the spinal column;

a plate with a base mountable to the vertebra, the plate also having a tongue protruding from the base with an end distal to the base and two sides perpendicular to the end, the plate also having a groove formed by a top of the base and inner edges of the two sides of the base, wherein the tongue and the groove are directed in opposite directions along the long axis of the spinal column; and a plate with a base mountable to the vertebra, the base having two sides, a top and a bottom, the plate having a first groove formed by the top of the base and inner edges of the two sides of the base, the plate also having a second groove formed by the bottom of the base and inner edges of the two sides of the base, wherein the first groove and the second groove are directed in opposite directions along the long axis of the spinal column, wherein each plate slidably interconnects with the adjacent plate(s) when attached to the vertebrae, the interconnection occurring at (a) the two sides of the tongue of one of the interconnecting plates, and (b) the inner edges of the two sides of the other of the interconnecting plates.

* * * * *